US008457725B1

(12) United States Patent
Fischell et al.

(10) Patent No.: US 8,457,725 B1

(45) Date of Patent: *Jun. 4, 2013

(54) ALARM TESTING AND BACKUP FOR IMPLANTED MEDICAL DEVICES WITH VIBRATION ALERTS

(71) Applicants: David R. Fischell, Fair Haven, NJ (US) Angel Medical Systems, Inc., Fair Haven, NJ (US)

(72) Inventors: David R. Fischell, Fair Haven, NJ (US); Michael Sasha John, Larchmont, NY (US); Jonathan Harwood, Rumson, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/633,275

(22) Filed: Oct. 2, 2012

Related U.S. Application Data

(63) Continuation of application No. 12/461,877, filed on Aug. 27, 2009, now Pat. No. 8,301,231.

(51) Int. Cl.
*A61B 5/04* (2006.01)

(52) U.S. Cl.
USPC .......... 600/509

(58) Field of Classification Search
USPC .......... 600/508–527; 607/2, 115–116
See application file for complete search history.

(56) References Cited

U.S. PATENT DOCUMENTS

| | | | | |
|---|---|---|---|---|
| 6,112,116 | A | 8/2000 | Fischell et al. | |
| 6,272,379 | B1 | 8/2001 | Fischell et al. | |
| 6,609,023 | B1 | 8/2003 | Fischell et al. | |
| 6,774,769 | B2 | 8/2004 | Okada | |
| 7,801,596 | B2 | 9/2010 | Fischell et al. | |
| 8,269,634 | B2 * | 9/2012 | Fischell et al. | 340/573.1 |
| 8,301,231 | B2 * | 10/2012 | Fischell et al. | 600/509 |
| 2009/0072768 | A1 | 3/2009 | Murray et al. | |

* cited by examiner

*Primary Examiner* — Carl H Layno
*Assistant Examiner* — Paula J Stice
(74) *Attorney, Agent, or Firm* — Rosenberg, Klein & Lee

(57) ABSTRACT

An implanted device which includes a vibrator having a drive motor and a drive circuit. An accelerometer is connected to the vibrator and senses alarm test data related to the displacement of the vibrator. A power source provides electricity to the implanted device and a processor is configured for bi-directional wireless communication. The processor is configured for receiving a command from an external device for performance of an alarm test and the processor analyzes the alarm test data for generating test results.

21 Claims, 11 Drawing Sheets

Table 1: Accelerator measurement of vibration

| Test Case | Motor ON Interval | X Axis | | | | Y Axis | | | | Z Axis | | | |
|---|---|---|---|---|---|---|---|---|---|---|---|---|---|
| | | Max | Min | Delta | Delta as % of Full Scale (255) | Max | Min | Delta | Delta as % of Full Scale (255) | Max | Min | Delta | Delta as % of Full Scale (255) |
| 1 | 10 ms | 171 | 149 | 22 | 8.63 | 132 | 116 | 16 | 6.27 | 132 | 127 | 5 | 1.96 |
| 2 | 20 ms | 184 | 137 | 47 | 18.43 | 145 | 103 | 42 | 16.47 | 132 | 127 | 5 | 1.96 |
| 3 | 40 ms | 196 | 124 | 72 | 28.24 | 159 | 91 | 68 | 26.67 | 133 | 126 | 7 | 2.75 |

Table 2: Accelerator measurement of vibration baseline vs. motor-on period

| Test Case | Motor-On Interval | Delta: Base | | | Delta: Motor-On Period | | |
|---|---|---|---|---|---|---|---|
| | | X-axis | Y-axis | Z-axis | X-axis | Y-axis | Z-axis |
| 1 | 5-MS | 1 | 2 | 1 | 3 | 6 | 2 |
| 2 | 10-MS | 1 | 1 | 1 | 17 | 24 | 8 |
| 3 | 15-MS | 1 | 1 | 1 | 33 | 42 | 7 |
| 4 | 20-MS | 1 | 1 | 1 | 51 | 55 | 8 |

FIG.5

ALARM TESTING AND BACKUP FOR IMPLANTED MEDICAL DEVICES WITH VIBRATION ALERTS

REFERENCE TO RELATED APPLICATION

This Application is being filed as a Continuation application of Ser. No. 12/461,877, filed 27 Aug. 2009, now issued U.S. Pat. No. 8,301,231.

FIELD

The invention is in the field of implantable medical devices that provide patient notification. The invention is particularly relevant to implantable cardiac devices that emit vibration alerts when selected cardiac conditions are detected.

BACKGROUND

Implantable medical devices that monitor ambulatory patients must have a manner of alerting patients to relevant events. Notification can occur for the detection of medical events such as acute ischemia, arrhythmia, bradycardia, or low levels of insulin. Notification can also be triggered by the detection of low battery levels, device malfunction, signal quality issues, and when device adjustment is merited. In order to provide patient notification the implanted medical device (IMD) can use either internal or external alerting means, or both. In the case of internal alerting, the IMD can use, for example, vibration or sonic alert signals. In the case of external alerting signals, the IMD may communicate with an external device which then produces an alert signal such as a vibrotactile, sonic, or visual signal. Multimodal alert protocols occur when the alert signals are emitted to relay information to multiple sensory modalities.

It is useful to provide both internal and external alerting for medical devices because this increases the likelihood that the patient will pay attention to the alert signal and take appropriate action (e.g., going to the hospital in the case of an emergency alarm related to a dangerous cardiac condition). However, in the daily life of a patient the IMD may not always successfully communicate with the external device. For example, the patient may leave the external device beyond the IMD wireless communication range. Additionally, when the patient is in the shower or swimming an external device is not practical and alert signals may not be noticed by the patient. Further, the external device may not work correctly as may occur if its battery becomes depleted. In these cases it is important that at least internal alerting is available to notify the patient to a serious medical event. Accordingly, it is important to be able to determine that the IMD can successfully provide alerting to the patient.

Vibration alarms have a number of advantages. In the case of both internal and external alarms, patients may prefer relatively silent vibration alarms over sonic alarms that may cause persons nearby to learn about a particular medical condition which is being monitored. In a movie theater visual and auditory alarms may be inadvertently ignored due to saturation of these sensory channels, while there is little interference with respect to noticing a vibration alarm.

Alert transducers may fail in several manners. This is particularly true in the case of a vibration alert which requires moving parts. A transducer may simply fail to operate or may operate in a compromised manner. In the case of vibration, the vibration may be provided at a lower vibration level or frequency than intended. If an electric motor that provides the vibration is not able to product the expected strength, frequency, or pattern associated with the alert signal, then the patient may misinterpret the alert, become unsure as to whether an alert is occurring, or simply not experience it at all. Accordingly it would be an advantage to provide a manner of objectively testing the integrity of alarm signals such as vibration alarms.

Subjective reports of vibration have a number of disadvantages. Older people or diabetics may experience lower levels of vibration due to physiological factors rather than to actual mechanical changes which occur in the motor. If the patient complains that a vibration alarm is not strong enough, a medical professional may pursue different solutions depending upon whether the problem is with the patient or the implanted device. Accordingly would be an advantage to provide a manner of objectively assessing the strength of the alarm signals such as vibration alarms.

Additionally, if a patient fails to respond to an alarm such as when the patient is sleeping, the medical professional may not be able to determine whether the alarm strength was inadequate for the patient and must be increased, or whether the IMD did not actually vibrate as anticipated (or at all!) at the time of the alarm. It would be an advantage to provide a manner of objectively determining if an alarm occurred, and that it occurred as intended, at the time that the actual alarm was triggered. An alarm log of what actually occurred can be valuable both for clinical and legal reasons.

Lastly, when changes in alarm characteristics are small, and alarms occur infrequently (e.g. not more than every 5 months) then a patient may not be able to subjectively assess whether the vibration alarms have changed from how they originally experienced these. Vibrotactile sensitivity for internal vibration signals changes as a function of vibration pattern, frequency and amplitude. It is important to be able to accurately measure any changes which may occur in the IMD's vibration signals so that these can be detected, quantified, and/or compensated for if desired.

The IMD can be any type of implantable medical device. In one embodiment the IMD is a cardiosaver device, as described by Fischell et al in U.S. Pat. Nos. 6,112,116, 6,272,379 and 6,609,023, incorporated herein by reference, which can detect a change in the patient's electrogram that is indicative of a cardiac event, such as acute ischemia and then provide notification. The IMD can also be a medical device which provides drug or electrical stimulation to a neural, vagal-nerve, or other anatomical target. The IMD may be partially implanted, such as an implanted insulin pump/delivery system with an external reservoir. Notification (or alerting/alarming) occurs by way of an internal alarm system within the IMD and/or an external alarm system which may comprise an external, pager-type device, a patient programmer, and a remote station where patient data may be sent for review. The IMD communicates with the external alarm system using wireless communication signal as long as the external alarm system is within range. The external alarm system of the current invention has capabilities equivalent to those described by Fischell et al in U.S. Pat. Nos. 6,112,116, 6,272,379 and 6,609,023. For example, the external alarm system may provide one or more types of visual, sonic and vibratory alerting signals, and may provide voice/data communication between the IMD/patient and a remote medical monitoring station.

The IMD and/or the external alarm system may provide a single type of alarm. Alternatively, at least two types of alarms may be used ("two stage alerting"). In one embodiment a major/critical event alarm (an "EMERGENCY ALARM") can provide notification of the detection of a serious medical event (e.g., a heart attack which is an AMI) and the need for immediate medical attention, and a less medically significant alert (a "SEE DOCTOR ALERT" or alarm) can signal the detection of a less serious condition that is not life threatening such as exercise induced ischemia or the detection of a depleted battery. The two types of alerting consist of different multimodal alarm patterns, which are selectable to occur at different strengths. When a particular sensory modality of alerting is used to provide notifications of different event types, the signals may differ in amplitude (e.g., strength of signal), pattern (e.g., long or short bursts, inter burst-interval), or frequency (e.g., a 500 or 2000 Hz sound). It would be helpful to perform various back-up/compensatory operations if the internal and external alerting did not occur as expected and to be able to quantify and detect these operational deviations. Transducer malfunction can cause normally distinct types of notification to be mistaken, or ignored, by the patient.

US patent application 2009/0072768, entitled "Use of an accelerometer to control vibration performance" to Murray el al. teaches using an accelerometer to measure the performance of a vibration motor and to increase, in a closed loop manner, the voltage applied to the drive circuit to compensate for changes in the speed of rotation that may occur over time. U.S. Pat. No. 6,774,769 to Okada entitled "Vibrating Alert Device" describes a method of increasing the voltage applied to a vibration alarm so that it increases gently over time and does not startle a user of the device.

SUMMARY

The invention provides systems and methods for assessing alarm characteristics related to medical notification. Alarm occurrence and characteristics of the actual transduced signal are measured objectively and automatically using alarm tests. This is especially relevant for implanted devices with vibration alerting. Device operation, including the alerting operations, can be adjusted as a function of alarm test results. Adjusting alerting operations can include assessing, controlling, or adjusting the operation of a vibration alarm of an implanted medical device, and also modifying the alerting operations in a manner that includes or excludes the use of vibration alerting.

A first aspect of the invention includes an implanted medical device having monitoring, detection, memory, communication and alerting capability. The alerting capability can be internal, external, or both. In the case of internal alerting the invention includes a vibration alarm capable of providing various patterns of vibration. Both internal and external alerting signals can be evaluated using alarm tests.

An alarm testing system can include a sensor (e.g., an accelerometer) that can sense a characteristic of a transduced alarm signal (e.g., in the case of a vibration signal the speed, displacement, amplitude, frequency, rise, or fall of the vibration may be measured). A processor can be configured for deriving and analyzing alarm test results. The alarm test results can include comparisons between the alarm test data and alarm test threshold criteria which can be used to determine if the alarm test yielded an 'alarm-pass' or 'alarm-fail' alarm test result. The processor is further configured to operate according to the alarm test result.

Alarm tests can be designed with relatively short test signals. A vibration test signal can be quick (e.g., 20 ms or less) so that this is unlikely to be noticed by the patient. Alternatively, the alarm test signals can be relatively long (e.g., 100 msec) which may occur at certain times of day, and which may be noticed by the patient in order to provide assurance to the patient that the device is working. Back-up alarm protocols are provided for instances in which an alarm test fails.

Performing periodic vibration alarm tests may decrease the risk that a motor component will reside continuously in a particular position and become biased against movement away from that position. The alarm tests provide periodic exercise for the transducer.

The described invention addresses the shortcomings of medical notification systems that do not monitor or test the notification transducers, and offers novel advantages by providing: objective and automated testing of the integrity of transduced alarm signals; objective quantification of the strength of the alarm signals; alarm test criteria that are adjusted based upon the programmably selected characteristics of the alarm; objective determination of whether an alarm occurred at a particular time and as intended in response to detection of medically relevant events; objective assessment of the types of changes in an alarm signal which may have occurred; programmable and selectable alarm back-up and alarm compensation operations; alarm back-up protocols which are initiated if an alarm in a particular modality experiences alarm failure. Further the invention provides the advantage, particularly relevant for vibration alerts, of testing an alarm transducer in a manner by which the patient does not become aware of this test.

These and other objects and advantages of the current invention will now be described in the description of the figures, the detailed description of the invention, and the claims.

BRIEF DESCRIPTION OF THE FIGURES

FIG. 5 shows Table 1 which includes a summary of data collected from the accelerometer for the X, Y, and Z axes during an alarm test for vibration where the alarm test signals ranged from 10 to 40 ms. Table 2 shows results for alarm test signals ranging from 5 to 20 ms.

DETAILED DESCRIPTION OF THE INVENTION

Figure 1:
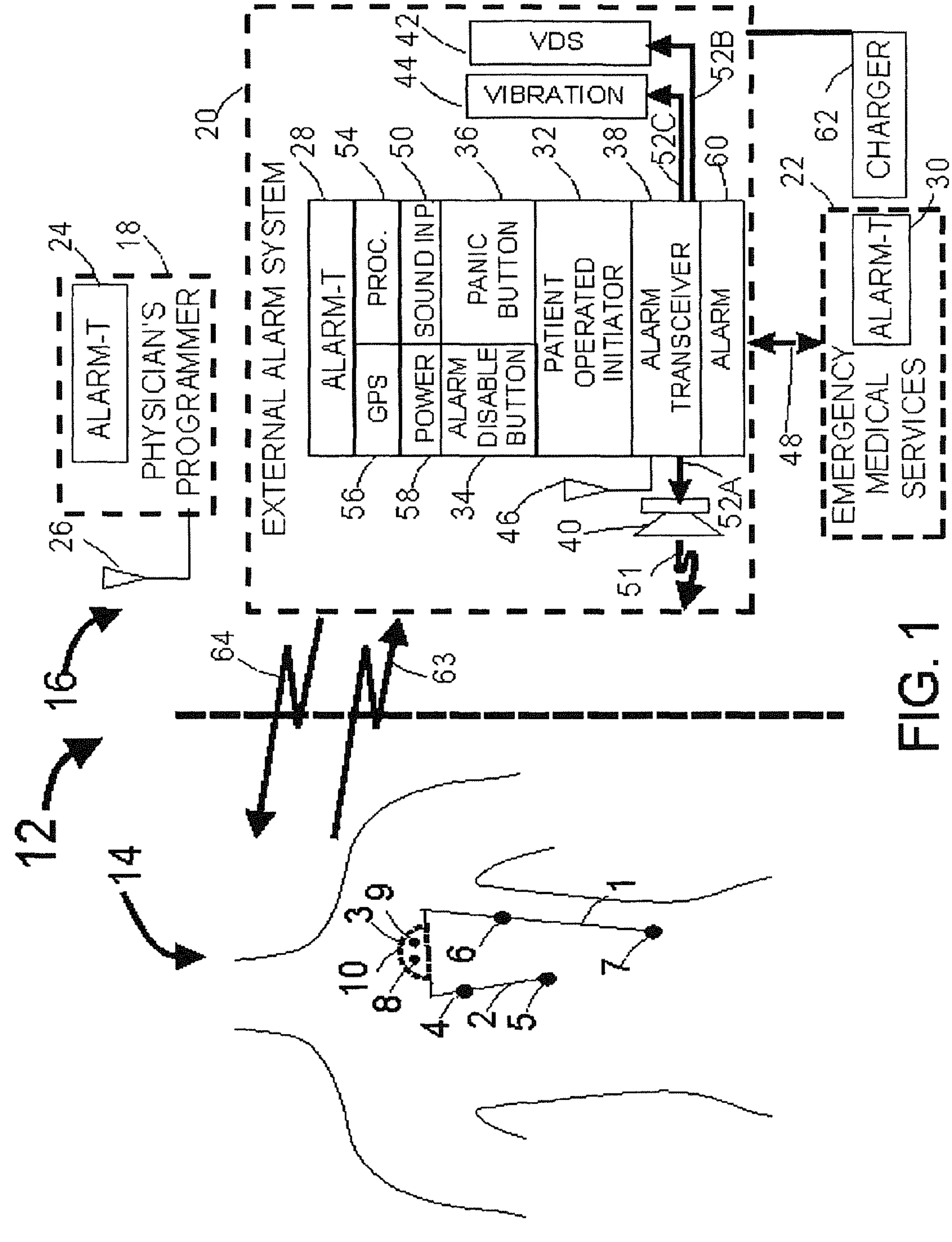
FIG. 1 illustrates a system for medical monitoring and for alerting a patient and/or remote monitoring station that a medically relevant event has occurred.

FIG. 1 illustrates an example of a medical system 20 including internal components 14 and external components 16. The IMD 3 includes sensors to monitor a condition associated with a patient. For example, electrode contacts can act as sensors to measure cardiac activity, neural activity, or other electrical activity of the body. A microphone sensor can measure sonic data related to the patient (e.g. cardiac or respiratory sounds), an accelerometer can measure movement, acceleration or position, and a biosensor can measure metabolite levels within the patient. In one embodiment, an insulated electrical wire lead 2 can include sensors, and can connect with the IMD 3 using an IS1 connection to communicate with battery-powered sensing electronics contained within an IMD housing 10. The lead 2 can be configured with sensing electrode contacts 4 and 5 which can be placed subcutaneously or within the heart. Each lead may incorporate one electrode contact or as many as sixteen contacts. Housing contacts 8 and 9 could be situated within the surface of the IMD housing 10 without any wire leads extending from the IMD 3. The IMD 3 can include a stimulator realized as an insulated electrical wire lead 1, having stimulation contacts 6 and 7, which communicates with battery-powered stimulation electronics of the IMD 3. Contacts 8 and 9 (as well as 4, 5, 6, and 7) can be configured to provide stimulation, sensing, or both. Stimulation can also be used to provide an electric tickle for alerting purposes.

In one embodiment the lead 2 in FIG. 1 could contain a sensor that is advantageously placed through the patient's vascular system and into the apex of the right ventricle in order to monitor cardiac activity. The lead 2 may have a sensor attached to contact 5 such as a pressure or optical sensor which is implanted to sense signals from the digestive system in order to monitor activity related to digestion. The sensor could also be a glucose sensor that is used to measure glucose levels of a patient, or an electrode that is placed in a patient's brain in order to sense neural activity. When the contact 5 is configured with a sensor, lead 2 has independent wires for communicating power and data between the sensor and the circuitry of the IMD 3.

FIG. 1 also shows external equipment 16 that consists of: 1. a physician's programmer 18; 2. an external alarm system EXD 20 which may be implemented as a pager-type device, a desktop unit, or both; and, 3. a 3$^{rd}$ party such as a remote medical center 22. The physician's programmer 18 has 2-way wireless communication 26 for communication between the programmer 18, the IMD 3 and the EXD 20. The external equipment 16 provides users with the capability of interacting with the IMD 3, for such operations as programming and retrieving data from the IMD 3. The external equipment 16 also provides external alarm signals when the IMD 3 notifies the external equipment 16 that an alert should be issued.

Figure 4:
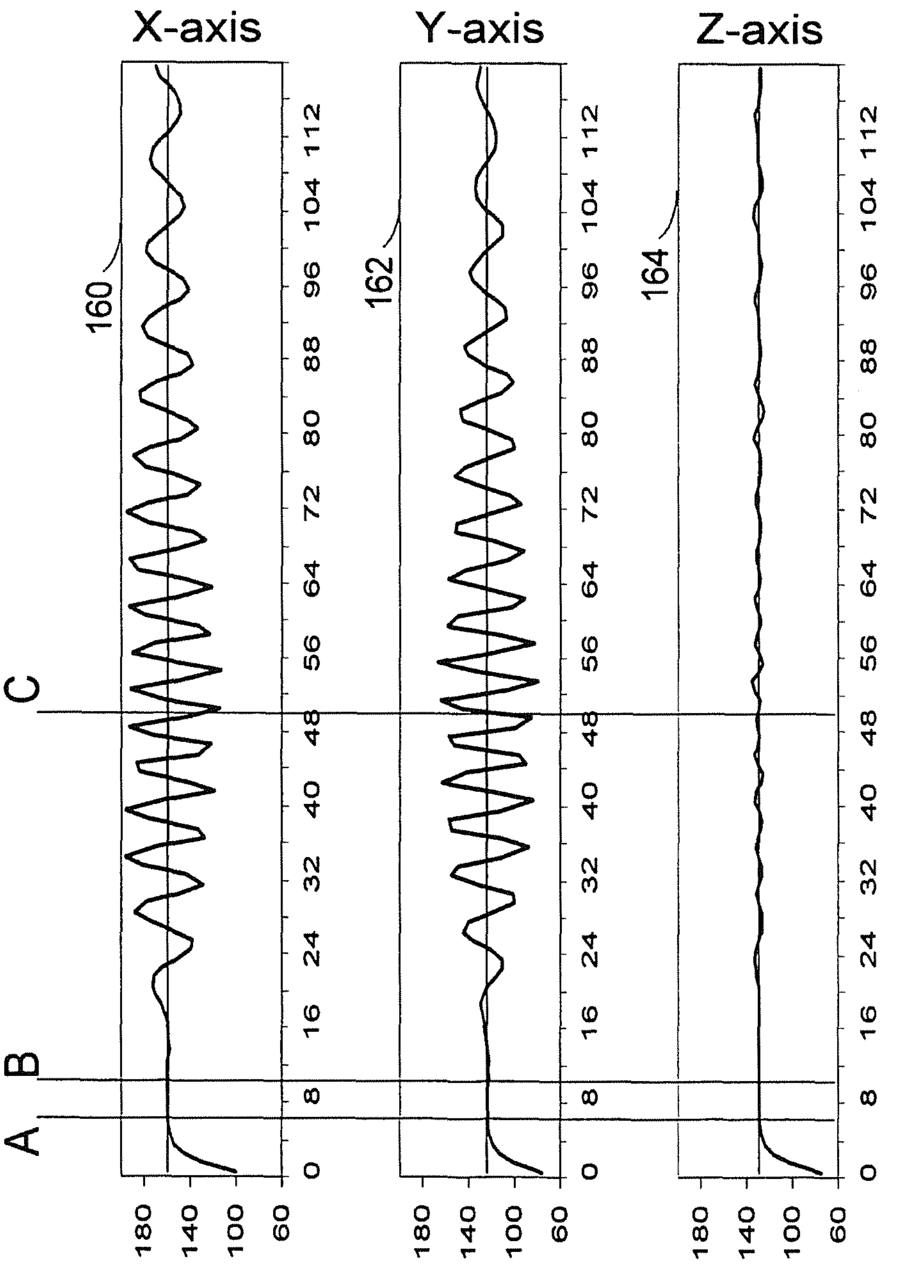
FIG. 4 shows the 3 graphs of data collected from the accelerometer for the X, Y, and Z axes during an alarm test for vibration using a 40 ms test signal.
Figure 7:
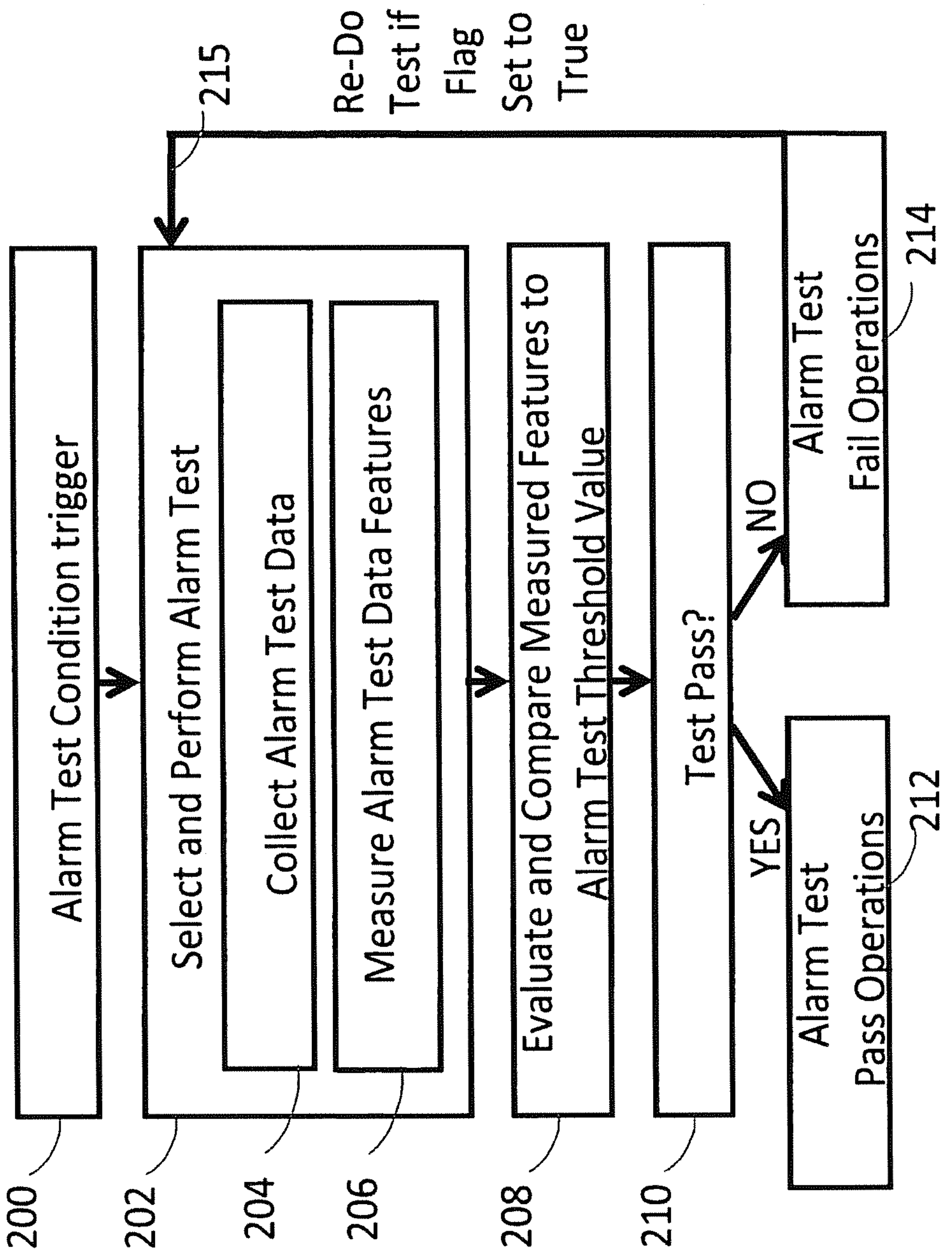
FIG. 7 is a flowchart of a method for performing an alarm test and operating according to an alarm test result, according to an example embodiment of the present invention.
Figure 8:
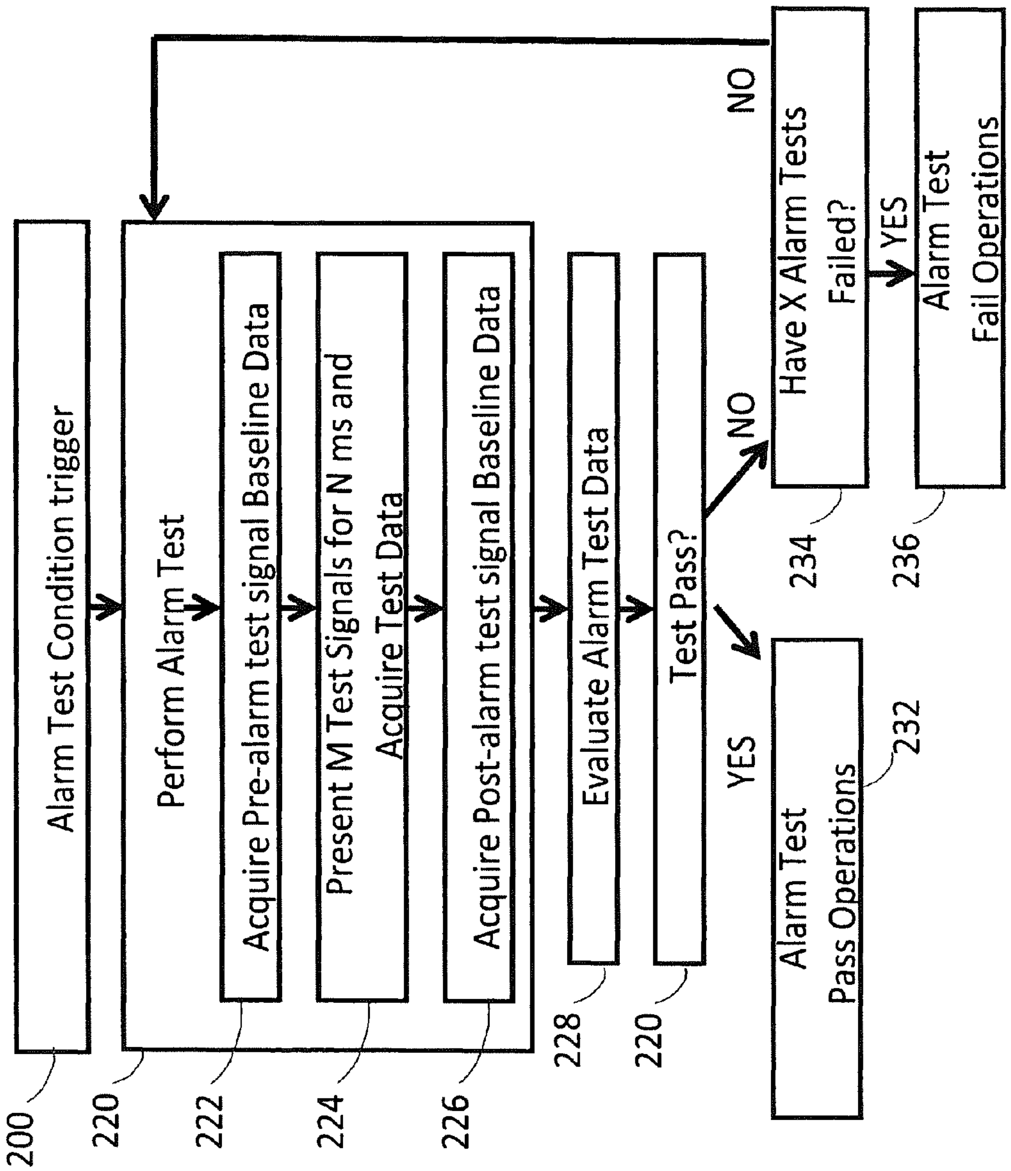
FIG. 8 is a flowchart of an alternative method for performing an alarm test which uses baseline data derived from pre-vibration and/or post-vibration data, and operates according to test results, according to an alternative example embodiment of the present invention.
Figure 9:
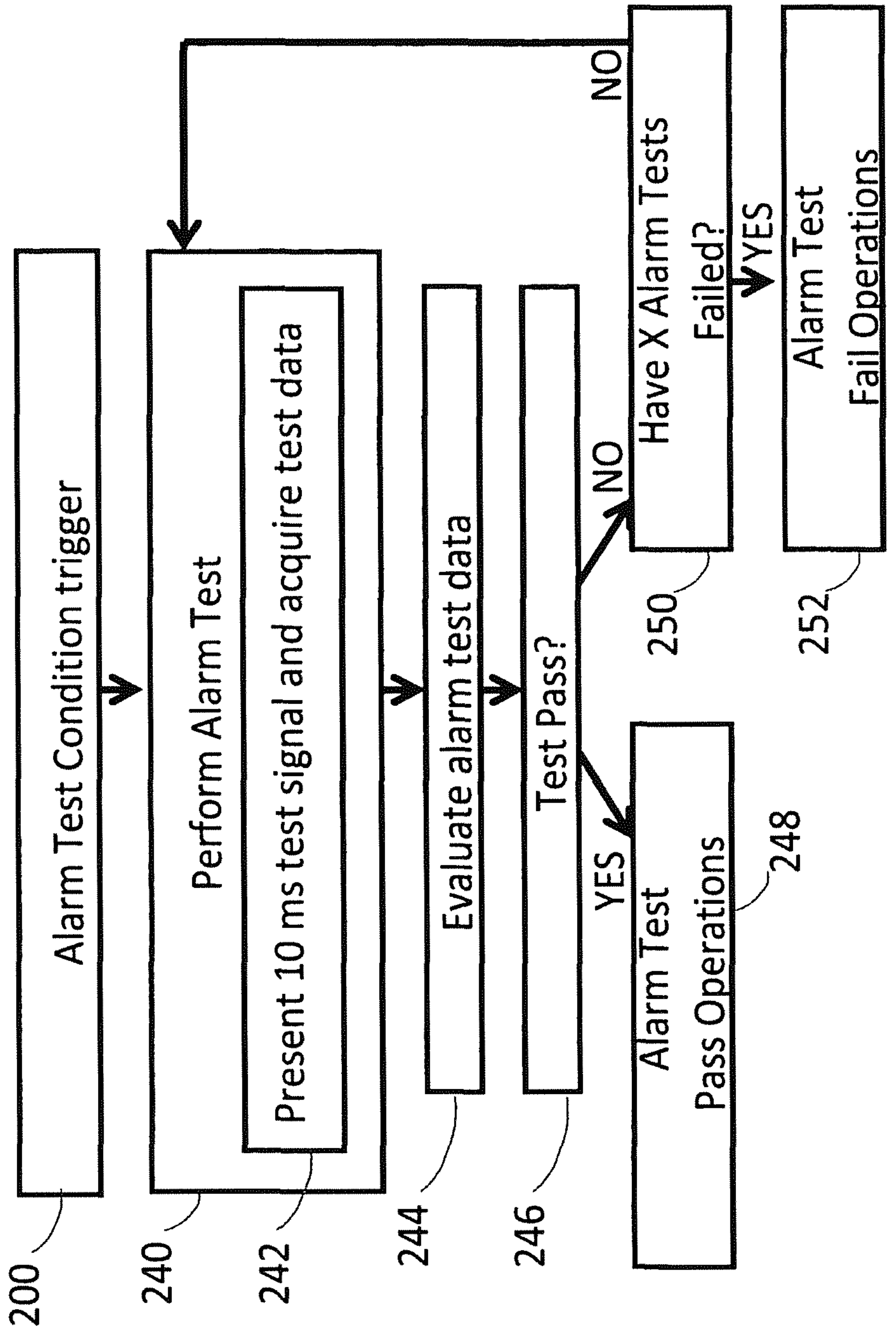
FIG. 9 is a flowchart of an alternative method for performing an alarm test which specifically uses a sub-threshold pulse of 10 ms, and operates according to test results, according to yet another alternative example embodiment of the present invention.

The programmer 18 shown in FIG. 1 can be used to program the IMD 3 in order to adjust parameters and information related to, for example, data collection, event detection, data storage, alerting protocols, and alarm tests. The programmer 18 can send a wireless signal 64 to the IMD 3 and it can also receive an incoming wireless signal 63 sent from the IMD. The programmer 18 has an alarm test module 24 which provides functionality related to alarm testing. The alarm test module 24 can be configured to command the IMD 3 to perform an alarm test and to return the test results. For example, the IMD 3 could be told to perform a vibration alarm test for 100 ms at a particular vibration level and a vibration parameter (e.g. amplitude) could be measured. This value could be sent to the programmer 18 as an alarm test result. The test results received by the programmer 18 can be processed by the alarm test module 24, such as by comparing the test result to an alarm test criterion to see if the test passed. The alarm test module 24 can also create an alarm-test event log(e.g., alarm test parameters and results) which can also include historical alarm test information that was uploaded from the patient's IMD 3. This log will contain both alarm test results for tests initiated by the programmer 18, as well as tests done during normal operation of the IMD 3, and this information will be coded appropriately. Examples of the alarm tests initiated by the alarm test module 24 are shown in FIGS. 7-9, where the alarm test condition trigger is the command sent from the programmer 18. The alarm test module 24 also has software routines that provide the medical professional with an interactive graphical display for viewing and or measuring alarm test results (e.g. a cursor which can measure a characteristic of a waveform produced as part of an alarm test such as seen in FIG. 4) and for programming the IMD 3 with alarm test parameters such as test times or intervals and the test signal characteristics. The alarm test module 24 also permits medical professionals to adjust protocols stored in the alarm test module 28 of the EXD 20, alarm test module 30 of a 3$^{rd}$ party such as remote medical services 22, and alarm module 120 of the IMD 3. For example, protocols can be adjusted to set parameters for the back-up alarms that occur if a particular alarm signal is not transduced successfully. The alarm-test module 28 of the EXD may be provided with some or all of the features described for the alarm-test module 24 of the Programmer 18. Additionally, the two modules 24 and 28 may operate jointly and are configured with routines that allow these modules to synchronize or update each other's information and parameter settings when this is defined as part of an alarm-test protocol or as implemented by a medical practitioner or other user who operates the devices 18, 20. The remote medical station 22, may run software routines which allow remote interfacing with the two alarm-test modules 24, and 28 in order to obtain information or set parameters as may be required by an individual patient's monitoring needs. The remote medical station can communicate with the alarm module 120 of the IMD 3 directly, but will usually do this indirectly through communication with devices 18, 20.

In FIG. 1, the EXD 20 has a patient operated initiator module 32 which can provide a button that allows for the initiation of communication between the EXD 20 and the IMD 3, an alarm disable module and button 34, a panic module and button 36, an alarm transceiver 38 with communication and drive circuitry, a speaker 40, a visual display system module ("VDS") 42, a vibration module 44, and a communication circuit 46 such as can be used to provide near-field and far-field wireless communication (e.g., Zarlink, cellular, line-based modem). The communication circuit 46 allows data transmission to and from medical services 22 via the communication link 48. The EXD 20 has a sound input module 50 having a microphone and associated electronics for providing (along with the alarm transceiver 38 and speaker 40) two-way voice communication with remote medical services 22. The sound input module 50 is also configured to measure the sound emitted by the speaker 40 in order to ensure that the sound level is within specified bounds as part of an alarm test for the sonic alarm.

The VDS 42 of EXD 20 may include 1 or more colored diodes which are activated when a particular alarm type is triggered. The VDS 42 may also include a display screen for displaying waveforms related to sensed data, graphical and text fields related to the functioning of the IMD 3 or EXD 20 or information about what caused an alarm. The VDS 42 may include a navigation button which can be used to navigate through menus and to select desired menu options presented by the VDS 42. Alternatively, the VDS 42 may contain a touch-sensitive display screen which allows for user input. The VDS 42 can cooperate with the alarm test module 28 to present the user with options which allow the patient to perform alarm testing of the IMD at will. If the patient places the EXD 20 within range of the IMD 3 and initiates and alarm test, then the EXD 20 will send a wireless command to the IMD 3 to perform an alarm test such as is shown in FIG. 7. When specified in an alarm-test protocol stored in the alarm module 120 of the IMD 3, the IMD will then communicate the results of the alarm test back to the EXD 20 and these can be analyzed, stored, or displayed by the VDS 42 in collaboration with the alarm test module 28. Upon receiving alarm test results the EXD 20 can emit a sonic or visual message of test success (e.g. 2 beeps of 1500 Hz, 3 seconds of a blinking yellow LED, or a text message indicating "alarm test passed") while in the case of alarm test failure the alarm test module 28 will cause the EXD 20 to display messages, or do other operations, as defined in an alarm-test protocol for an alarm-test fail result.

The alarm test module 28 of the EXD 20 is capable of performing an alarm test within the EXD 20 itself. If the alarm test is for a vibration alarm then the alarm test data can be collected by an accelerometer or a microphone of the vibration module 44, if the alarm test is for a sonic test then the test data will be collected by a microphone of the sound input module 50. A visual alarm test can be performed by a light sensor placed adjacent to the VDS 42 such as the LEDs. Each modality should be tested in the case of the EXD 20 since some of the alarm modalities may not work well in all environments. If the patient is hard of hearing or is listening to the TV loudly then the visual cue may be the first alarm signal that is noticed by the patient.

If an alarm notification is sent from the IMD 3 to the EXD 20, via the 2 way communication modules 46, 118 then the alarm transceiver 38 can provide alarm signals 52A-C to the loudspeaker 40, the VDS 42, and/or a vibration module 44 to warn the patient that an event has occurred. Under the control of the EXD processor 54, the alarm transceiver 38 provides the alarm signals as defined in the alarm protocols of the alarm module 60. In this manner, notification is provided and patient input responses, or other operations, which occur in response to the alarm are managed. Examples of external auditory alarm signals 51 include a periodic buzzing, a sequence of tones and/or speech which may be a pre-recorded message that instructs the patient as to what is happening and what actions should be taken or which may be real speech communicated by medically trained practitioners at the remote station 22.

When the detection of a life threatening event (e.g., AMI or tachycardia) is the cause of the alarm, the EXD 5 could automatically notify medical services 22 that a serious medical condition has occurred and an ambulance could be sent to treat the patient and to provide transport to a hospital emergency room or catheterization clinic. If communication with medical services 22 occurs, the message sent over the link 48 may include at least one of the following types of information as previously stored in the memory provided within the EXD's processor 54 or as directly uploaded from the IMD 3: (1) What type of medical event has occurred, (2) the patient's name, address and a brief medical history, (3) a GPS coordinate and/or directions to where the patient is located (using the GPS satellite or cellular grid information as per GPS module 56), (4) patient data, historical monitoring data, and the data that caused the alarm (5) continuous real time data as it is collected after the alarm, and (6) alarm test protocol parameters and test results for the IMD 3 or EXD 20.

The processing modules 84 and 100, of the EXD 20 and IMD 3 contain a real time clock or timer and other components which are normally available in the processing modules of current art implantable devices, portable smart-devices and pagers. Further, in a preferred embodiment, the EXD 20 is realized using a smart-phone (e.g., as made by Apple, Blackberry or Palm), which may be implemented using specialized software and/or smartcards. The individual modules may be implemented in hardware or software and contains all of the necessary components to implement alarming of the patient and/or remote station. When the EXD is realized using a 3rd party device, the keyboard or other buttons can be assigned to operate identically to input means provided on a specialized EXD 20 device.

The patient operated initiator module 32 provides useful capabilities. For example, by pressing a particular button of the initiator module 32 (or navigating to a menu item of the VDS 42), the patient can initiate the transmission of data from the IMD 3, through the EXD 20, to a medical practitioner at the medical services 22. This can allow a patient to selectively choose and tag data in the IMD which is then sent to a medical practitioner. For example, the patient can be told to press a button to send data when the patient experiences a particular symptom such as dizziness. The alarm disable module and button 34 can be used by the patient to turn off an actual alarm of the IMD 3 and/or EXD 20. After and alarm signal is stopped by the patient, reminder alarm signals can be issued periodically to remind the patient that an alarm occurred. The patient might press the panic button 36 in the event that the patient feels that he is experiencing a severe medical event even in the absence of IMD 3 or EXD 20 alarm notification. The EXD 20 may use a charger 62 to recharge a rechargeable power supply 58 of the EXD 20.

The components of system 20 are configured to cooperate in order to enable alarm testing to occur. The IMD 3, EXD 20, physician programmer 18, and remote monitoring station 22 are designed to provide the alarm testing to occur and the results to be reported and evaluated so that alarm test results may guide operation of the system 20 in the case where alarms are not transduced as intended. Each component of the system 20 has an alarm test module which allows it to participate in alarm testing in order to provide this functionality to the system 20.

Figure 2:
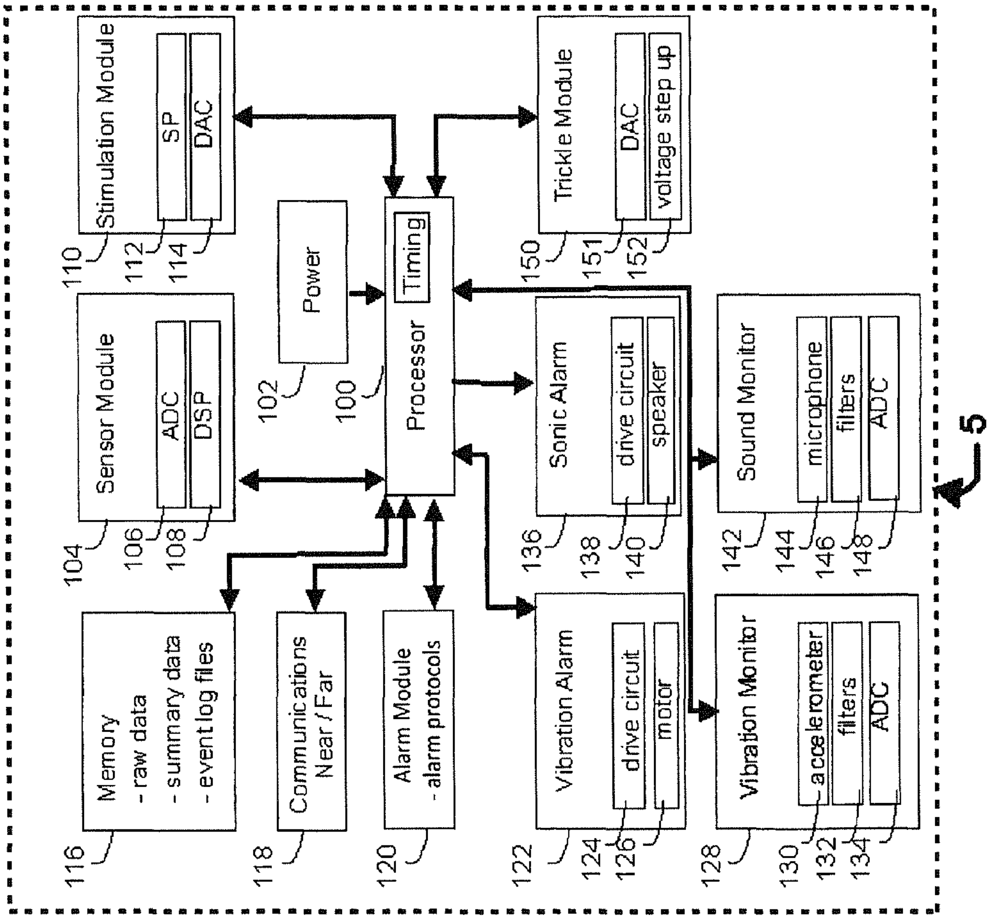
FIG. 2 is a schematic diagram of the components of an example embodiment of the implanted medical device.

FIG. 2 is a block diagram of an embodiment of the IMD 3 shown in FIG. 1. The IMD 3 includes a processor module 100 which is powered by a power module 102, having a power supply that may be rechargeable and contain means for receiving inductive charging. The modules of the IMD 3 are functionally connected so that communication and power is provided thereby allowing monitoring, patient alerting, and/or therapy to occur under control of the processor module 100. The processor module 100 operates the sensor module 104 to obtain sensed data from sensors such as provided by lead 2. Sensed data can be amplified and conditioned by the analog-to-digital (ADC) circuitry 106 and may be further conditioned by means of digital-signal-processing (DSP) circuitry 108. The processor module 100 can also process the sensed data and then measure selected features of cardiac data (e.g. R-wave height, average ST-segment voltage, ST-segment duration). The processor operates the stimulator module 110 in order to stimulate the patient. Lead 1 could be operated to provide cardiac pacing or defibrillation. The stimulation signal can be created by signal-processing (SP) circuitry 112, which may include an arbitrary function generator, and can then be amplified by the digital-to-analog (DAC) circuitry 114. The processor module 100 can use the memory 116 to store raw, feature, and summary data and an event log. The event log can contain times of events that are detected by the processor. The log can further contain various relevant events such as alarm test results. The memory 116 may be accessed by the processor module 100 in a manner that allows it to function as a query-capable database. If the processor module 100 analyzes the sensed data and detects a medical event which has been defined as requiring patient notification, it may do so as defined by the alarm module 120. Notification may include operating the communication module 118 to attempt to communicate with external devices. The communication module 118 permits 2-way communication between the IMD and external devices and is configured for both near field and far field (e.g. Zarlink) communication.

If an event occurs for which notification is needed, the processor module 100 will utilize the alarm module 120 in order to select the associated alarm protocol for the particular event. If the alarm protocol uses a vibration component, the vibration alarm module 122 operates its drive circuit 124, to power a motor 126 and cause movement (e.g., rotation). The motor 126 may be either an AC or DC motor and the drive circuit 124 can utilize a frequency generator, voltage gate, or other electronic means in order to generate the alarm signal that drives the motor. The drive circuit 124 may also contain circuitry configured to measure the impedance of the motor 126, either instantaneously, at one or more particular defined moments in time, or integrated over time. The processor 100 may determine that the motor is not functioning normally if the measured impedance/resistance value fails to meet alarm test threshold criteria defined in the alarm module 120, causing an alarm test failure. This may cause the processor module 100 to record an error message/alarm-fail alarm test result in the IMD memory 116.

The vibration monitor module 128 contains an accelerometer 130 which can be MEMS-based and which preferably measures motion along orthogonal X, Y and Z axes. Alternatively a piezoelectric sensor (e.g., single-axis accelerometer, microphone, electret-based monitor, or other sensor capable of measuring pressure changes) can be used which is capable of measuring a characteristic of the motor's vibration along at least one axis. An ADC module 134 samples the output of the accelerometer 130, preferably at 2-4 times the frequency at which the motor vibrates. Preferably, in the case of a 250 Hz vibration, the ADC should be sampling at a minimum of 1000 Hz. Filters 132 may be applied to the output of the accelerometer 130 if this is an analog output in order to remove energy from frequencies outside the range of interest of the vibration measurement. The filters 132 can also be implemented digitally on the output of the ADC 134. The resulting digitized waveform represents vibration test data and can be used to measure characteristics such as the frequency or amplitude of vibration (displacement). Alternatively, measurements can be made upon the analog waveform without digitization.

Sonic alarms are provided by the sonic alarm module 136 which contains a drive circuit 138 that powers a sonic transducer 140 such as a piezoelectric speaker. Components that may provide this capacity include crystal and ceramic based piezoelectric diaphragms, piezoelectric sounders, and piezoelectric buzzers such as those provided by Murata Manufacturing Co., Ltd or Omega Piezo Technologies, Inc. The sound monitor module 142 contains a sound measurement sensor module 144 such as an electret, MEMS-based, carbon-based, or piezoelectric-based microphone. An ADC module 148 samples the output of the speaker 140, preferably at 2-4 times the frequency of the highest tone. However, if the sonic signal is 4000 Hz, the ADC may operate at 1000 Hz if its sampling is time-locked to the acoustic signal. In this example every $4^{th}$ peak of a 4000 Hz sign wave carrier will be measured by the ADC. This will provide an acceptable measure of sound pressure level for a 4 kHz tone since the aliased energy will fit exactly into the ADC sampling rate wave maxima coinciding with the timing of the samples of the ADC buffer. Filters 146 may be applied to the output of the speaker 130 or can be implemented digitally.

Electric tickle alarm capability is provided by the tickle module 150 which contains a drive circuit 152 that can include voltage-step electronics to increase the voltage (e.g., 3 volts) of the implanted power system 102 to higher ranges. Alternatively, the tickle module 150 can contain a separate power supply module designed to provide short-duration high-voltage power. This may be realized by a $2^{nd}$ rechargeable battery which is powered off of the primary power supply 102. Use of an electric tickle has been previously described in Fischell et al U.S. Pat. No. 6,272,379. The electric tickle can be delivered by the housing of the IMD 3 to which the output of the tickle module 150 is directed, or via electrodes 8, 9 in the housing, or via a subcutaneous lead 1 which has been positioned to provide a tickle warning rather than to stimulate an area cardiac tissue.

In the medical system 12 multiple types of events can cause patient alerting to occur. Most relevant to medical monitoring, alarms occur when the processor 100 detects a medical event in the sensed data that is defined as requiring an alert. The alert may be provided by the vibration module 122, the sonic module 136, the tickle charge module 150, or a combination of these which occur simultaneously, sequentially, as a backup in the case of a particular type of alert failure, or as otherwise defined in the alarm module 120. In addition to, or instead of, the internal alarm signals provided by the IMD 3, the IMD can communicate with external devices 16 in order to provide external alarming. Patient alerting can occur if the processor determines that the power supply is below a specified threshold. Notification can also occur if the processor module 100 determines that there is a problem in the sensed data (bad data quality or unexpected changes in the measured features). Additionally, patient alerting can occur if the alarm protocol module 120 determines that an alarm test command was sent from the physician programmer 18 or the EXD 20 and was received by the communication module 118. During normal operation, alarm tests will usually occur when clock values of the processor module 100 match times scheduled for alarm testing.

The medical system 12 of the current invention requires at least three processes to occur successfully during patient monitoring: a medical event must be detected by the IMD 3, the patient must be notified of the event through an alarm, and the patient must notice the alarm (so that the patient can understand its significance and respond appropriately). If the medical event is detected but the patient is not successfully alerted then the device does not provide any benefit. Ensuring that alarms can occur in the future have occurred, as intended, and providing appropriate operations or backup alarms in the case where an alarm doesn't occur as intended is realized in the current invention using alarm tests. Since a primary method of patient alerting uses a vibration alarm, an example of how this test is performed is now provided.

Vibration Alarm Test:

Alarm testing can be accomplished by the IMD 3 in order to measure vibration characteristics such as the magnitude of a vibration for a test signal. The physical configuration of the IMD motor 126 in relation to the vibration monitor 128 module may vary. The motor and sensor may be glued to each other or arranged separately within the IMD 3. In this example the two components were connected to a circuit board within the IMD 3 via a flexible cabling arrangement. The accelerometer module 130 may be connected directly to the IMD 3 circuit board or may reside upon foam or other dampening material.

The alarm tests which will be described tend to use very short alarm test pulses, such as between 5 ms. and 40 ms. Providing vibration alerts is one of the largest uses of energy in an implantable device. Using very short vibration tests may therefore be of great advantage. For example, if the motor was tested for 10 ms once a day, every day of the year, the total activation time would be 10 ms*365 which is only 3650 ms (i.e., 3.65 seconds). Even if one wanted to test the motor for 100 ms, and for the test to be repeated 4 times each day, then this would lead to a total activation time of 100 ms*4*365 which is only 146 seconds (i.e., little over 2 minutes of vibration per year). An important advantage of the disclosed alarm testing is that it can be implemented without depleting much energy from the IMD 3 battery 102.

An alarm test may include a single test signal or test results may be derived from a series of test signals. For example, test signals may be presented once per second for 3 seconds and measured to observe repeatability. While the accelerometer may only measure vibration along one axis, the one used here (ADXL330) outputs data for all three axes (X, Y, Z) which were sampled simultaneously and digitized at 1 kHz. The time of the processor module 100 can be used for triggering the test signals and the ADC 134 may be interrupt based and synchronized. The steps of the test may be executed by the IMD 3 processor 100 as follows.

1. Enable accelerometer 130 and start 1 ms timer. Timer's expiry initiates ADC conversion.
2. Start reading ADC 134, and extract 8 most significant bits (MSBs) which are stored in arrays X[N1], Y[N1], Z[N1], where here N1=120 samples, which are collected for each axis and serve as a "sample set" of alarm test data. Sample sets can be stored in the buffers of the ADC 134 or can be sent to the memory module 116.
3. Collect N2 values of the sample set. These are discarded since the accelerometer circuit requires time to stabilize. In this case N2 can equal 10 samples, since about 6 ms is needed for the accelerometer to reach stability after it is activated. In FIG. 4, the asymptote between time=0 and the vertical bar labeled "A" shows this warm-up.
4. Activate motor 126 with an alarm test signal defined in alarm module 120 that lasts for N3 ms, which in this case is 40 ms (period defined between times B and C in FIG. 4).
5. Apply brake, such as a reverse polarity signal, after N4 ms (not done here).
6. Finish collection of sample set until the arrays of 120 values are full.
7. Stop timer and ADC conversion.
8. Repeat again after delay if alarm test protocol is defined to use more than one alarm test signal.
9. Operate processor module 100 to evaluate alarm test results by comparing alarm test data to vibration threshold criteria defined in the alarm module 120 to generate an "alarm test pass result" or "alarm test fail result".

Figure 3:
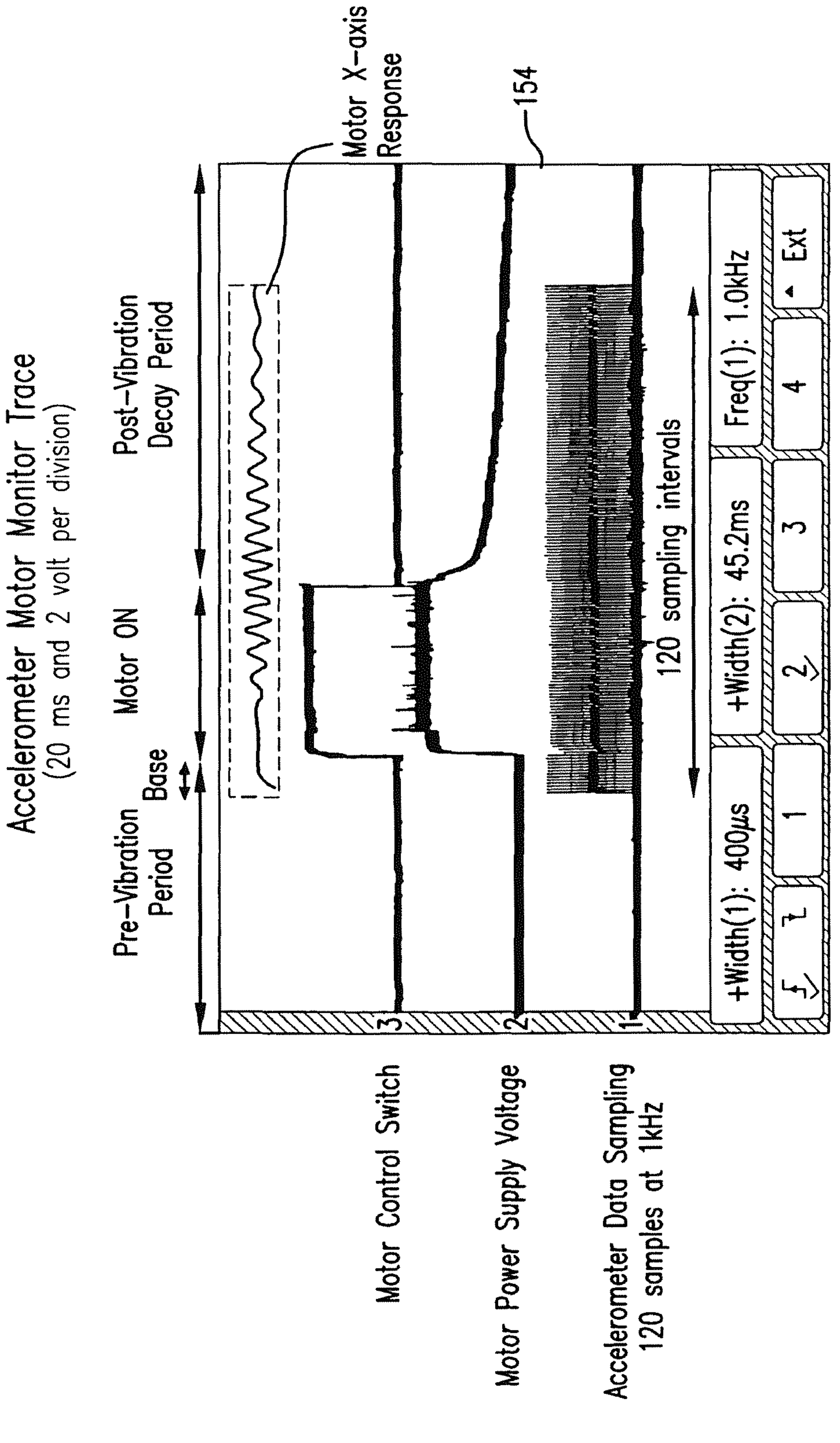
FIG. 3 illustrates an oscilloscope screen with tracings obtained during an example of an alarm test which used an accelerometer to measure vibration, and also has a superimposed trace of the accelerometer output.

FIG. 3 shows measurements, as set of captured oscilloscope traces on an oscilloscope screen. As labeled on the left side of the figure, the traces were related to the data sensed on the motor control switch, the voltage supply applied to the motor (i.e., the alarm test signal), and the ADC sampling of the accelerometer output (i.e., sampling times for the alarm test data). An N3=40 ms pulse served as the alarm test signal. During the period labeled "pre-vibration period the voltage applied to the motor is zero. During the first 10 samples of the accelerometer ADC (bottom row), the test signal voltage applied to the motor remains off. Since the accelerometer requires 6 ms to stabilize, this leaves the last 4 samples to serve as "pre-vibration baseline" reference values (associated with time-period labeled "Base"). The next 40 ADC samples record the vibration during the "Motor On" period where the test signal was supplied from the drive circuitry 124. These are the "alarm-on" data values which will likely produce the largest values of Table 1. Lastly there are 70 samples collected after the alarm test signal is halted (termed "decay data" values). The actual values for the X-axis that were output by the accelerometer are shown in a plot at the top of FIG. 4, but are also superimposed on the top of the oscilloscope screen ("Motor X-axis Response") in order to show the relationship of the vibration to the test signal that was applied. After alarm-test signal termination, the relatively slow dampening of the vibration causes a substantial signal to be maintained for about 20 msec. This profile may be partially due to a slow decay of the power supply as could be due to discharge of the capacitor as well as the choice not to apply a break pulse to stop the motor.

FIG. 4 shows the accelerometer output for the x, y, and z axes in graphs 160, 162, and 164, respectively, after 1 kHz ADC. The x-axis of each plot labels the 120 samples, with 1 ms inter-sample interval, and the y-axis scale range has 256 values derived from the 8 bit ADC buffer. Vertical bar "A" shows where the accelerometer functionally comes online (it takes 6 ms to warm up). Bar "B" shows where voltage of the alarm test signal was first applied to the motor 126. Bar "C" marks the termination of the alarm test signal. The alarm test data samples that fall between A and B serve as the pre-vibration reference values. The values between B and C are the motor-on alarm test data. The data collected from C to the end of the recording are the decay-period alarm test data. The alarm test signal produced vibration along the x- and y-axes, roughly in similar magnitude suggesting a circular rotation as opposed to linear or elliptical, while the z-axis recorded only slight vibration, as expected.

Several characteristics of the alarm test data can be used to assess vibration including: a. vibration strength which may be measured as the maximum or minimum amplitude or the difference between the two; b. average vibration strength which may be vibration strength measured across a particular interval such as for 15 ms prior to end of the alarm test signal (e.g. time denoted by "C"); vibration rise, which may be measured as the time to reach maximum vibration strength from the start of the alarm test signal or the slope as the vibration strength increases over a selected period such the first 20 samples; vibration decay which may be measured as the time needed for the amplitude to decrease to a specified vibration strength such as 50% of the average "Motor On" value, or which may be measured as the slope of vibration strength decrease across a selected interval (e.g., the first 20 samples after the motor is turned off); vibration frequency which may be measured as the maximum, or average, number of zero crossings across a specified interval such as a portion of the motor-on interval. For example, in the x-axis plot 160, the average frequency from the $36^{th}$ and to $64^{th}$ sample (i.e. 28 samples) is computed from the 7 zero crossings obtained using a 1000 Hz sampling rate. In this case, the frequency is 250 Hz (i.e., 7*(1000/28)).

FIG. 5 provides alarm test data summaries from three alarm test signals (test pulses of 10, 20 and 40 ms) in Table 1. The full scale value was 0-255 (8 most significant bits). "Delta" is a vibration strength measure calculated in this example as the difference between the maximum and minimum values recorded within each X, Y and Z dataset. Deviations from a mean value represent positive and negative excursions due to vibration movement in opposite directions. Due to the particular physical configuration (orientation of accelerometer to motor), the x-axis was most sensitive to motor vibrations although only slightly more than the y-axis, while the z-axis showed almost not change. In order to provide a useful alarm test, the test pulse sent to the motor must activate the motor "long enough" to produce a delta measure that can be distinguished from a specified strength-threshold criteria value when the motor is working correctly. When the motor is not activated, the accelerometer "at rest" has a delta which remains under $\leqq 3$ for any axis during the pre-vibration Baseline interval (labeled "Base" in FIG. 3). Even using a 10 ms pulse signal, a minimum delta of 16 (seen in y-axis) was found. Accordingly all three pulse durations, although very short, were more than adequate to be used as an alarm test signal during an alarm test. By calibrating the ADC units, the values of 0-255 can be converted into units of force, displacement, or otherwise, and the alarm tests can be calculated upon these units rather that simple ADC values.

Figure 6:
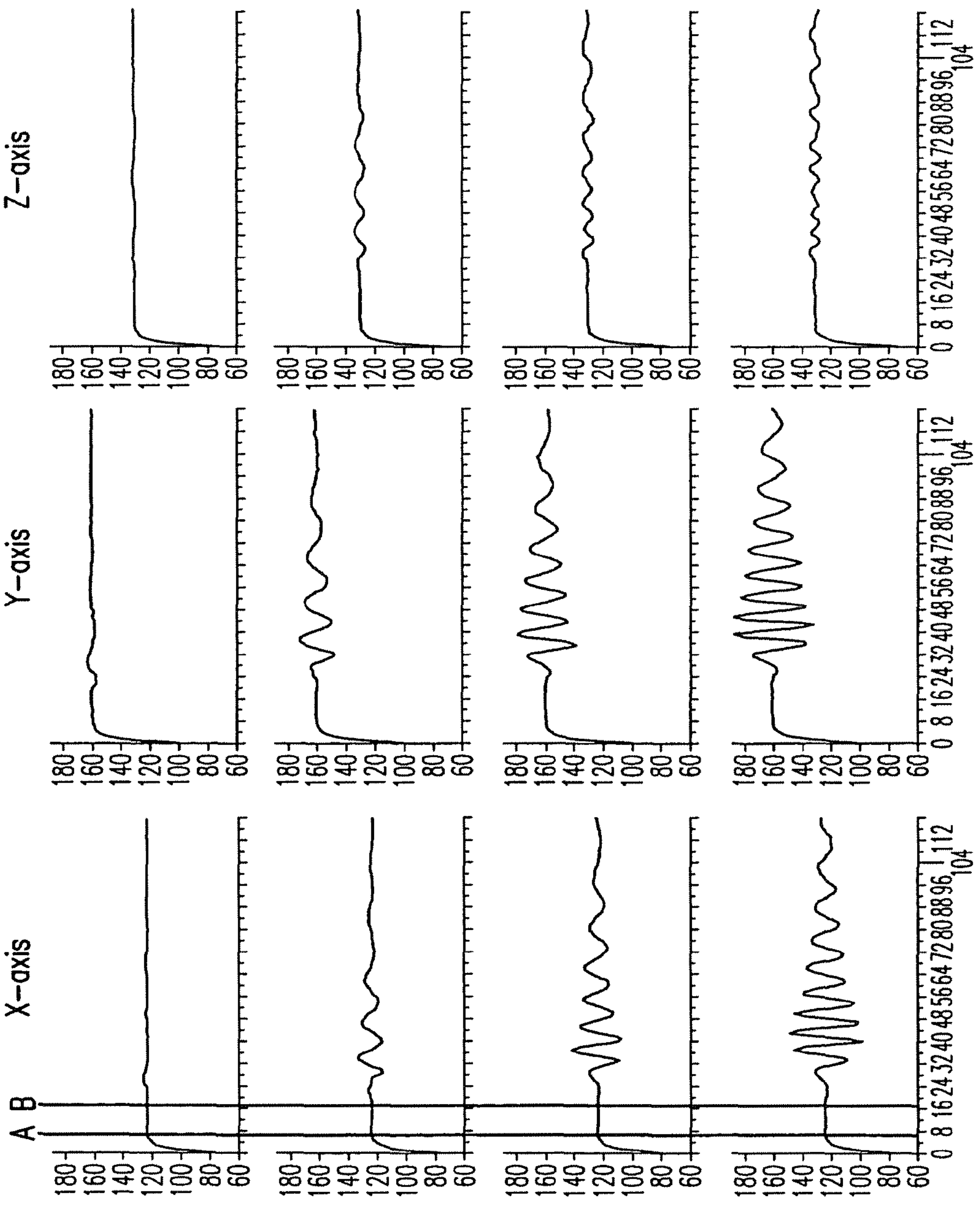
FIG. 6 shows 4 rows of data collected from the accelerometer for the X, Y, and Z axes during alarm tests for vibration using test signals ranging from 5 ms (top row) to 20 ms (bottom row).

Table 2 of FIG. 5 provides alarm test data summaries from four alarm test signals (test pulses of 5, 10, 15 and 20 ms) which produced the alarm test data shown in FIG. 6. FIG. 6 shows 4 rows of data collected from the accelerometer for the x-, y-, and z-axes during vibration-based alarm tests using test signals ranging from 5 ms (top row), 10 ms ($2^{nd}$ row), 15 ms ($3^{rd}$ row), and 20 ms (bottom row). The period between A and B was increased so that the Base interval contained 10 (sample 6 to sample 16) rather than 4 values. Although visual inspection of the top row of FIG. 6 indicates that the 5 ms pulse did not really produce a visually noticeable oscillation, Table 2 indicates that the x- and y-axes delta values were larger than the z-axis delta, as well as the corresponding intra-axis Base delta values. However, if features of the alarm test data such as "vibration frequency" are to be assessed as part of the alarm test then the 5 ms pulse was likely too short to serve as an alarm test signal given the particular motor and accelerometer used to conduct this type of vibration-based alarm test.

Illustrative Alarm-Test Embodiments

In one embodiment, the cardiac monitoring system 12 for monitoring a human patient utilizes an IMD 3 that has a primary patient alerting means which operates an alerting module such as a vibration module 122. An accelerometer 130 is configured to sense movement of the device in at least one direction during an alert-test. Additionally, the device has a sensor 5 configured to operate with sensing circuitry 104 for sensing signals from the patient's heart. The device's processor module 100 is configured to detect abnormalities in the signals from the heart, to alert the patient by actuating the primary patient alerting means (e.g. 122) following detection of abnormalities in the signals from the heart, and also to perform at least one type of alarm test, which can be defined in the alarm module 120. The selected alarm test 202 can include both actuation of the primary patient alerting means for at least one defined test interval and also measurement 206 by the processor module 100 of alarm-test data sensed 204 by the accelerometer 130 during the test interval. The alarm test also includes operating the processor 100 to detect whether sufficient or insufficient movement of the vibrator occurred during the test interval 208, and to produce alarm test results which can include quantity measures of characteristics of the movement such as magnitude and frequency. The implanted device also contains a wireless communications system 118 for communicating with external equipment 16 which, in turn, has wireless communication circuitry 46 designed to receive signals from the implanted medical device. The cardiac monitoring system also has a secondary patient alerting means (e.g., 136) which is designed to notify the patient when insufficient movement is detected. The alarm test can be performed at defined inter-test intervals, if the wireless communications system receives a "perform alarm-test command" from the alarm-test modules 24, 28, of the external equipment, or can be performed contingently upon the detection of abnormalities in the signals from the heart, when the actual alert signal is provided, and in that manner can serve to trigger a back-up alarm when the primary alarm fails 214. The secondary patient alerting means can be internal or external, and can include establishing a care-link session accomplished in conjunction with a remote station 22 and can include alerting a remote medical professional 22. Since communication with remote stations are a type of notification, the alarm tests can include communication between the EXD 20 and the remote services 22, and this can be configured so that the remote services is notified that the incoming message is simply an alarm test rather than a real event. The schedule for testing communication-based alerting may be different for that which occurs while testing the IMD 3 or EXD 20 transducers.

It should be noted that the monitoring system can use an IMD 3 that has a first internal patient alerting sub-system that generates at least a first internal alarm signal that can be, for example, a vibration signal. As long as at least one sensor is configured to sense actuation of the first internal patient alerting sub-system and a sensor is provided for sensing data that is used to calculate a medical condition of the patient, then the system 12 can provide medical monitoring and also perform alarm tests. The device's processor module 100 or the EXD processor 54 is configured to detect abnormalities in the patient's medical condition, actuate the first internal patient alerting sub-system following detection of abnormalities in the patient's medical condition and also perform an alarm test. The alarm test can include both actuation and measurement of the first internal patient alerting sub-system during a test interval so that the processor evaluate the alarm test data to detect whether the alarm signal was sufficient or insufficient. In the case where the alarm signal was insufficient, then an alarm-test fail operation can occur such as operating a secondary patient alerting sub-system to generate a second alarm signal which notifies the patient when insufficiency is detected in the first internal alarm signal. Since the device has a wireless communications system 118 and external equipment 16 with wireless communication 26, 46 designed to receive signals from the implanted medical device, the second alarm signal can include communication sent to, or from, a remote party (e.g., a central station or physician), or both.

Illustrative Alarm Test Protocols.

FIG. 7 shows an example method of operating the IMD 3 to perform an alarm test and then to operate according to the alarm test results. Step 200 is the initiation of an alarm test by an alarm test trigger condition being evaluated as true. Alarm trigger conditions can include, for example: a "perform alarm test" command sent from an external device 16 and received by the communication module 118 of the IMD 3; or, the detection of the occurrence of a clock time, tick count, or periodic interval (e.g., 1 month) by the processor module 100 which has been defined in the alarm module 120 as requiring the performance of an alarm test. A "perform alarm test" command can also occur if a patient initiates an alarm test, for example, by pressing an associated button on the EXD 20.

In step 202 an alarm test protocol is selected from the alarm module 120 according to the type of test condition that triggered the alarm and is performed under control of the processor module 100 which causes an alarm module 122 or 136 to provide an alarm and causes a monitor module 128 or 142 to collect and digitize the alarm test data. In step 206 the processor module 100 measures features of the alarm test data. In step 208 the alarm test data features are compared to at least one alarm test threshold criterion. In step 208, the processor can evaluate any alarm test data which is available from steps which can include: evaluating a feature measured in the current alarm test data; obtaining the results of comparisons between alarm test data and alarm test criteria; adding or comparing current alarm test data to historical values of alarm test data; and, computing statistical or trend summaries from the current and historical alarm test data. In step 210 one or more operations and comparisons which occurred in step 208 are evaluated in order to determine if the alarm test passed or failed.

In the case of alarm test success, alarm test pass operations 212 occur. Alarm test pass operations 212 can include, for example, sending a test pass result to the alarm module 120 and updating the event log in the IMD 3 memory 116. The alarm test event information sent to the event log can include, for example, the time of the test, the type of test signal which was used, the test results which can simply include a pass/fail result or also may include one or more measurements associated with the test. The alarm test event log stored in memory 116 may retain only the most recent alarm test results or a defined number of prior results as well.

In the case where the alarm test failed, then alarm test failure operations 214 occur. Alarm test failure operations 214 can include, for example: sending a test failure message to the alarm module 120 and updating the event log in the IMD 3 memory 116. Additionally, especially in the case where the alarm test has been defined to occur as part of an actual alarm triggered by the detection of a medically relevant event, one or more further alarm test failure operations which are defined in the alarm test module 120 can be implemented by the processor 100. These options can include, for example: 1. Changing the manner in which subsequently sensed data is stored in memory; 2. Halting the attempted provision of the type of alarm which failed the alarm test; 3. Storing alarm test data, measured features, and the alarm failure time in event log; 4. Repeating an alarm test with a different test signal; 5. Operating according to an alarm test failure protocol which continuously or otherwise attempts to communicate with the EXD 20 to provide an external alarm; and, 6. Providing an alternative type of alarm signal, in a different modality, which has been defined to be used contingently upon failure of an alarm test.

Option 1, listed in the foregoing, is advantageous because if patient alerting does not occur correctly then the IMD 3 may run out of memory for storing data related to relevant medical events which are detected. Various memory storage strategies can be used such as decreasing the duration of the samples which are collected (e.g., using 5 second rather than 10 second electrogram strips when storing samples of cardiac data), changing the protocols related to decimation of data prior to storage, changing protocols relied upon when stored data is over-written to make room for new data, etc. Option 6 is an extremely important solution to alarm failure because if the alarm test trigger condition was the detection of a medically relevant event, then the alarm test will function to identify a faulty alarm and will serve to provide a backup alarm so that the patient is notified successfully. The alarm failure operations can be selected and programmably defined to be based upon the type of event that triggered the alarm test.

The alarm test can be used to determine if the alarm signal was transduced successfully by the vibration or sonic module 122,136 and to perform selected operations in the case where the alarm test fails. An alarm test failure may include the fail operation step 214 of causing the IMD 3 to send a "See Doctor" alert to the EXD 20 and to note the specifics of the alarm test failure such as test time and test results.

Alarm tests must be able to occur accurately within a medical device that has been implanted in an ambulatory patient. Since the alarm test of FIG. 5 was done with an IMD 3 situated on a workbench rather than using an IMD 3 which was implanted in a person, possibly the variance of the Base period might be larger in actual practice when a patient is moving around. There are several possible alarm test protocol solutions that address the issue of isolating the portion of accelerometer values which are related to patient movement from those related to the intended measurement of vibration signal of the alarm being tested. The following protocols utilize different strategies for performing the alarm tests. Features and principles disclosed in each of these protocols can be combined and extended into more complex alarm test protocols.

Stable Baseline Protocol:

In this aspect of the invention, the alarm test protocol can require that the base delta values remain within a specific range, for example, less than an absolute level such as 10, or a relative level such as 20% of the maximum expected value during the test, in order for the alarm test to be valid. The requirement can be evaluated in step 208, and if this is the case than a flag can be set indicating that a stable baseline criterion was not met. This flag may cause the test to fail in step 210, and an alarm test fail operation which is defined in step 214 causes the alarm test to be redone no more than a maximum number of times prior to declaring a final failure, causing the alarm test protocol to change, or operating in an otherwise defined manner. This protocol is also practicable within the alarm-test paradigm illustrated in FIG. 8.

Inter-Axis Protocols:

Another solution is to use an alarm test protocol that compares data between different axes. A characteristic of vibration such as magnitude is evaluated by comparing the x- or y-axis delta with the z-axis delta, which should be low since the z-axis is normally orthogonal to the motor's vibration. Since patient activity is unlikely to map only upon a single axis, the differential between the 2 axes is likely to be related to motor vibration rather than specifically to patient movement, and therefore can be used as an alarm test measure. It may also be beneficial to compare data relative to the z-axis for other reasons. As shown in Table 1 of FIG. 5, an increase from 10 ms to 20 ms to 40 ms causes increases in x-axis delta of 25 (i.e. 47-22) and 25 (72-47), respectively. This is an increase of 114% (47/22) and 53% (72/47) with a doubling of intensity, and an increase to 227% (72/22) over the full range. In the case of comparing the x-axis to the z-axis which is used as a reference then the doubling of intensity causes an increase to infinity for the first step (47-22/5-5), and an increase to 2400% ((72/22)/(7-5)) across the full range. These are much larger changes those that seen when data from within a single axis was used and compared to a baseline interval of the same axis. Accordingly, in step 208, the alarm test threshold criterion may require that an x- or y-axis delta be a specified amount larger than the z-axis delta.

Sequential Test-Signal Protocols:

A third type of alarm test protocol compares alarm test results obtained from two or more different alarm test signals tested sequentially. If the test signals are the same signal then the features measured from the two sets of alarm data should be within a specified range in order for the alarm test to avoid being flagged and result in alarm test failure during step 208. Additionally, if the two alarm test signals are different (e.g. two different alarm strengths) then in step 208 the difference measured in the in the two sets of alarm test data can be compared to an expected difference such as the difference reference value obtained from an alarm test done in a medical professional's office after the IMD 3 was first implanted. The alarm test threshold criterion would be defined to ensure the difference between the vibration strength measured in response to the two alarm test signals of the present alarm test did not differ from the difference measured at the medical professional's office, by more than a specified amount.

Illustrative Alarm Test Types

In addition to different types of protocols that may be implemented to help ensure that the test results are stable (e.g. over time, with respect to a particular axis, or during a baseline or motor-on period), different alarm test types can be designed to achieve different advantages. The alarm tests can be conducted for different alarm modalities provided in the IMD 3 or the EXD 20.

Subliminal Alarm Tests:

An innovative feature of the invention is an alarm test which the patient does not notice, or which is barely noticed. This may be desirable so alarm testing does not interfere with the patient's daily life. One manner for accomplishing this is to use a very rapid alarm test signal. In the case of a vibration alarm test this may be a voltage pulse that lasts 10, 20, or 40 ms. Further, the alarm test may be scheduled to occur while a patient is likely sleeping (e.g., at 2 a.m.). In this case, the alarm test signal may be a pulse with a duration closer to 100 msec. An example of this type of test is shown in FIG. 9. Another type of subliminal alarm test may be realized by performing the alarm test whenever the IMD 3 provides patient alerting due to normal monitoring operations, rather than due to a scheduled alarm test. In a preferred embodiment vibration-alarm tests occur using the same vibration frequency which is used for providing real alarms to the patient. Alternatively, the vibration frequency used during an alarm test may be selected to be a different frequency, such as a frequency for which most subjects are less sensitive.

Assurance Alarm Tests:

Another innovative feature is to provide an alarm test which the patient notices and which occurs regularly in a patient's daily life. In the case of a vibration alarm test this can typically be a voltage pulse that lasts 100 ms, a pair of these pulses, or a particular pattern of pulses. The alarm test can be scheduled to occur every 24 hours at 12 p.m. (or only on Friday afternoon at 12 p.m.). When not corrected, daylight saving may cause this to occur an hour later during part of the year, and clock drift of the IMD may cause this time to shift slightly over time. Patients may like to have this feature because it assures them that the IMD 3 is working correctly and also it reminds them what the vibration feels like. Additionally, the IMD 3 could produce this vibration if the patient initiates this by operating the EXD 20 to send a "perform alarm test" command. Further, in one embodiment, a diagnostic test is run in the IMD 3 prior to performing the alarm test, and the test does not occur if there is problem in the IMD 3. In this case, the lack of an expected alarm test can tell the patient that a doctor visit may be necessary.

Alarm testing, for either subliminal or assurance alarm test types, can be triggered in step 200 by the EXD 20 sending an alarm test command to the IMD rather than the IMD 3 being programmed to do this automatically relative to its internal clock signal. One advantage of this approach is that the EXD 20 clock can be more easily adjusted when the patient is traveling so that alarm tests occur relative to a particular local time of day.

Quantitative Alarm Tests:

Another valuable type of alarm test is a test that enables a medical professional to easily determine if the IMD 3 is capable of providing an intended alarm at an intended strength. For example, if the medical professional causes a test alarm signal to occur during a patient visit, the monitoring modules 128, 142 can measure the strength of the alarm and can send data and quantitative measurements to the physician programmer 18 rather than simply a pass/fail result. Because the IMD 3 is implanted it is difficult to objectively measure the vibration or sound strength using external devices. The strength of the alarm as sensed by an external device applied to the patient may not provide very accurate objective assessment of alarm signal strength and may be influenced by the amount of tissue between an external sensor and the IMD 3. Additionally, it may be difficult for a patient or medical professional to simply feel or listen to the IMD's alarms and subjectively determine that the strength is 10 or 20% lower than it should be. In the case where a patient may be a diabetic and may have peripheral neuropathy it may be difficult to distinguish between when the patient is having a sensory deficit or when the alarm is not working as intended. Accordingly, alarm tests which quantify the size of a feature of the alarm data, rather than simply providing a pass/fail result are extremely advantageous in certain clinical situations.

Anticipatory Alarm Tests:

An alarm test may not only indicate the present capacity of an alarm transducer to provide an alarm but may also be able to anticipate a future failure of an alarm transducer. In the case of a vibration alarm, for example, the vibration rise time, plateau level, decay-time, decay-rate, decay interval required to reach ½ of the maximum vibration strength, as well as average frequency of vibration, and maximum frequency of vibration may all be used as an index of increased future risk of alarm failure. Prior to vibration failure, the motor may turn more slowly, or vibration strength may decay faster after the alarm test signal voltage is halted, due to increased resistance encountered by moving parts of the motor. This type of alarm test may cause the alarm protocol to be changed according to an alarm test failure operation 214. A type of protocol change which can be defined as an alarm test failure operation 214 can include increasing the strength or duty-cycle which is used to provide vibration pulses during an alert. In one embodiment, this type of increase will not cause the alert pattern to change and should only alter the strength of the vibration signal, while in a different embodiment the pattern of the alert signal itself may be altered slightly to compensate for motor-related issues. For example, 200 ms pulses may be increased to 250 ms in order to restore the intended strength of the vibration signal.

Check-Up Based Alarm Tests:

A further alternative is that the alarm tests can only occur every 6 months, or so, when the patient visits their doctor for a checkup. In this case, the alarm test routine can be defined to occur automatically as part of a device diagnostic routine that is run at that time, or as part of the data-retrieval routine so that the alarm test occurs automatically when patient data are uploaded from the IMD 3. Additionally, alarm testing can be defined to occur automatically, as part of the protocol whenever communication is established between the IMD 3 and the EXD 20. In this case, the results of the alarm test can be communicated to the EXD 20 or physician programmer 18 and are stored with the other information about the patient which is stored in the physician programmer 18.

Back-Up Alarm Tests:

A central feature of the current invention is the ability of the IMD 3 to identify if an alarm signal fails to be transduced successfully by the vibration, sonic, or tickle module and to provide an alternative back-up alarm signal in this case. In many circumstances, the vibration alarm 122 of the IMD 3 is preferentially relied upon by a patient, over other modalities, due to certain advantages. Vibration alarms can be felt even when the visual and auditory modalities are flooded with information as may occur if the patient is in a movie theater or restaurant when the patient alerting occurs. Vibration alarms offer advantages when the patient is hard of hearing, when the patient does not wish bystanders to know that the alarm has gone off due to medical privacy or other issues. Internal vibration alarms can be essential when the patient does not carry the EXD 20 near enough for an external alert to be triggered successfully. Other patients may prefer the sonic alarm, at least for certain alarm types. The alarm monitoring modules 128 and 142 can determine if the current alarm protocol is not successful and can select an appropriate backup alarm option so that the patient is successfully alerted. Although a patient may prefer an internal vibration alarm, the back-up alarm may be a loud auditory signal or electric tickle so that the patient is successfully alerted to a medically relevant event such as a heart attack.

In the case where the patient preference is only for external alarms to be used and the default alarm is realized through communication module 118 which contacts external devices 16, then backup internal alarms may be used. In one aspect, if the external devices do not send an acknowledgement that they received the alert notification, then the internal alerts can serve as the backup alarm option. In this case, the communication module 118 serves as its own monitor and can determine successful or unsuccessful alerting of external devices 16 via their acknowledgement of alert notification. Here the incoming communication data serves as the alarm test data. The feature of relevance in the measured data can be, at minimum, an ACK communication sent from the EXD 20. In the case of the tickle alarm, a voltage measurement device within the drive circuitry 152 can be used to monitor whether the tickle was delivered to the patient. Here the alarm test data which is collected in step 204 is a voltage or impedance data measured during the tickle and the alarm test threshold value might be compared to the integrated voltage level that was sensed during a specified interval. In step 214 operations occur which enable the patient to be notified when a default alarm does not occur as intended. In step 214, a back-up alarm protocol change can not only include changing from a vibration alarm to a sonic alarm, but also can entail increasing the volume of an auditory alarm which may have been set relatively low since it was assumed the patient would also experience IMD 3 vibration during an alert.

FIG. 8 shows another example method of operating the IMD 3 to perform an alarm test in which baseline data, which are acquired when alarm test signals are not presented, are compared data acquired while at least one alarm test signal is transduced. In the case of a vibration alarm a baseline interval of data can be used to assess the difference in the output from a monitor module 128 (e.g., an accelerometer in this case) between when the motor is active and passive. If a baseline period is used then this period may be obtained in a short period prior to motor activation, after motor cessation, or both. However as can be seen in FIGS. 3 and 4, since there is a relatively large post-alarm signal decay function that here lasts as long as the activation signal itself, it is likely better to only use the period before motor activation. Step 226 may be excluded when an alarm transducer is not actively damped (e.g. via electrical brake). Using values from 2 different axes, in which one axis is relatively not affected by the motor's vibration (e.g. the z-axis) while the other is altered by the motor's activity (e.g., the x or y axis) can allow the size of vibration to be assessed without using a baseline reference. However, in the case of a sonic or other type of alarm, or when vibration is measured along a single dimension by a pressure sensor (e.g. a microphone) then use of a baseline period will be necessary.

In step 200 the initiation of an alarm test occurs when a trigger condition is evaluated as true. In step 220 an alarm test protocol is selected from the alarm module 120 according to the type of test condition that triggered the alarm and is performed under control of the processor 100 which causes an alarm module 120 to provide an alarm and causes a monitor module 128 or 142 to collect and digitize the alarm test data. In step 222 the processor 100 measures features of the pre-alarm baseline data that was collected before the alarm signal is transduced, but after the monitor module has warmed up. In FIG. 3, this occurs during the period labeled base and includes 6 samples. In FIG. 6, this would be calculated on samples 6-16, since the base period was extended to 10 samples in order to get a more stable estimate of baseline values. In step 224 M test signals are presented for N ms each and alarm test data is acquired. If so desired a delay may be provided between each of the M test signals in order to cause the transducer to recover from the prior alarm signal, but this is not required. In step 226, post-alarm signal baseline data is collected, when specified by the alarm test protocol. Post-alarm baseline data can be obtained after each of the M test signals for example, when the transducer is actively damped, when sufficiently long interval is defined between M test signals, in order to measure a decay function of a transducer, or in the case of a sonic alarm when the transducer recovers quickly. Alternatively, step 226 may only occur after the last of the M test signals occurs. In step 228 the alarm test data is evaluated. This may include measuring selected features of the alarm test data, computing statistical measures from the alarm test data, combining alarm test data results, individually evaluating alarm test data from the pre-alarm and post-alarm baseline periods, and comparing at least one measured feature of the alarm test data to at least one alarm test threshold criterion. In step 228, the processor can evaluate any alarm test data which is available which can include: evaluating a feature measured in the current alarm test data, obtaining the results of comparisons between alarm test data and alarm test criteria, adding or comparing current alarm test data to historical values of alarm test data, computing statistical or trend summaries from the current and historical alarm test data. In step 220 the results of step 208 are evaluated in order to determine if the alarm test passed or failed. In the case of alarm-test success, alarm test pass operations 232 occur. In the case where the alarm test failed, then step 234 assesses if a selected number of failures have occurred and either repeats the alarm test by returning to step 220 or invokes alarm test fail operations 236. The alarm failure operations can be selected and programmably defined to be based upon the type of event that triggered the alarm test or the type of failure that occurred, or both.

In the case of an alarm test failure, the IMD 3 may send notification to the EXD 20 in step 236. The EXD 20 can be configured to respond to the IMD 3 in a number of manners that allows alarm testing to be customized by a patient or otherwise. For example, the EXD send an alarm-test command to the IMD 3 and ask that it re-run the test according from step 200, so that two test-failures must occur before the EXD 20 alerts the patient to an alarm-test failure. The EXD 20 or IMD 3 can be configured to run a sequential set of tests where the alarm-test signal is iteratively adjusted based upon alarm-test results in order to adjust for characteristics of the alarm test failure. In step 234, adjustments are made before returning to step 220. In this manner, the system 12 can permit a self-calibration and adjustment of the IMD alerts such as the vibration alert signal. Adjustments of the alert-signal may also be guided by, or require the approval of, a medical practitioner, which is a step that can be added to various locations of the method shown in FIG. 8. In addition, as has been disclosed, the EXD 20 can allow the patient to adjust the level of the alerts signals used in the IMD 3 and EXD 20. These adjustments may be restricted to a certain range, at least for decreases in vibration level. In any case, when the alarm levels have been adjusted by the patient, or otherwise, then one or more alarm-test criteria which are relied upon during alarm-tests must be adjusted in order to appropriately conduct the tests. For example, an alarm-test criterion conducted in step 208 of FIG. 8 may be selected from a lookup table stored in 116 or 120, based upon the alarm settings which have been selected by the patient. Accordingly, if a high-strength alarm has been selected then the criteria that are used during the alarm-test will be higher than those used to test a low-strength alarm level. This allows a back-up alarm, or other alarm-test failure operation, to occur only when the alarm-test results are different from those expected based upon the alert-level settings of the device.

FIG. 9 shows an example method of operating the IMD 3 to perform an alarm test which is specifically designed to be subliminal, in other words, it is unlikely to consciously be noticed by the patient. In step 200 the initiation of an alarm test occurs when a trigger condition is evaluated as true, which in this example can be the clock in the processor 100 of the IMD 3 indicating that it is approximately 2 a.m. and this time being defined in the alarm module 120 as a time when an alarm test occurs in each 24 hour interval. In step 240 an alarm test protocol is selected from the alarm module 120 according to the type of test condition that triggered the alarm and is performed under control of the processor 100 which causes an alarm module 120 to provide an alarm and causes an alarm monitor to collect and digitize the alarm test data. The alarm test signal is a 10 ms square wave pulse that is sent to the vibration transducer using the full range of approximately 3-4 volts available from the IMD 3 power supply 102. In step 244 the processor module 100 measures and evaluates features of alarm test data and compares the calculated value of delta with either intra-axis or inter-axis criteria, or both. Step 244 may include, for example, measuring selected features of the alarm test data, computing statistical measures from the alarm test data, combining alarm test data results, evaluating alarm test data from a pre-alarm baseline period, evaluating a rise or decay function of alarm strength, and comparing at least one measured feature of the alarm test data to at least one alarm test threshold criterion. In step 244, the processor can also evaluate any alarm test data which is available which can include: evaluating a feature measured in the current alarm test data, obtaining the results of comparisons between alarm test data and alarm test criteria, adding or comparing current alarm test data to historical values of alarm test data, computing statistical or trend summaries from the current and historical alarm test data. In step 246 the results of step 244 are evaluated in order to determine if the alarm test passed or failed. In the case of alarm test success, alarm test pass operations 248 occur. In the case where the alarm test failed, then step 250 assesses if a selected number of failures have occurred and either repeats the alarm test by returning to step 240 or invokes alarm test fail operations 252. The alarm failure operations can be selected and programmably defined to be based upon the type of event that triggered the alarm test or the type of failure that occurred, or both.

Alarm Test Signals.

The alarm test signals which are used may be pulses, ramps, sinusoids, or other types of signals. Additionally, more than one type of alarm vibration pattern can be tested in alarm tests conducted in a particular IMD 3. If the alert test signal is a voltage pulse that is used to drive vibration then the pulse may be a triangular waveform, or ramped pulse in order to cause the transitions between the on and off state to occur smoothly. If more than 1 alarm test pulse is used, such as may occur in a paired-pulse alarm test protocol, then the pulses can all have a particular voltage or may have different voltages. When different voltages are used, then any non-linear response of the motor which may be important could be detected. For example, the motor may work well at peak voltage, but not below that, causing a potential problem as the implanted battery ages or if non-peak voltages are used in the production of the actual alarm signals. If paired pulses are used, and longer pulse durations are selected as alarm test signals, then the pulse durations and inter-pulse intervals should be different that those used during actual alerting so that the test does not produce a pattern that the patient may be more likely to detect. The alarm module 102 may contain alarm test protocols that cause specified voltage patterns to be sent to the drive circuit 106 to cause the motor 126 to vibrate at an intended speed, frequency, or amplitude. When the motor is designed so that rotational speed is directly proportional to vibration frequency then the two terms become interchangeable.

Sonic alarm testing can occur for internal or external alarms that use sound. The alarm test signal can occur at lower intensity than sound used for actual sonic alert. One manner of testing transducers is to decrease frequency of the test signal sufficiently that it can be sampled by the ADC sampling rate. Accordingly, although a sonic alarm signal may occur using a 2000 Hz carrier frequency, the alarm test signal can be 500 Hz.

Threshold Criterion.

In addition to different types of alarm test protocols, various alarm test criteria can be used to ensure the alarm test is valid and to provide other advantages. It should be noted that the alarm test criteria can be selected or adjusted in relation to the settings being used by a patient. For example, if a patient's doctor has set their IMD 3 to use a medium vibration setting for providing notification then the alarm test uses threshold criteria which are set according to that setting. If the alarm notification was presented using a high vibration setting, then the threshold used by the alarm test would be larger. In this way, the settings for individual patients which are relied upon to provide actual alarms can be incorporated in to the criteria used to evaluate alarm test data.

Test Validity Criteria:

The alarm test protocol may implement a "feature consistency requirement". This type of criterion is helpful to ensure that the recorded motion is related to the alarm vibration rather than due to external forces. If this is the case then consecutive maxima or minima of the measured vibration waveform, across a specified interval should not differ beyond a specified amount. If this occurs, then the data can be flagged in step 208, and the test can be redone in step 214 by sending operation flow along path 215. It is unlikely that movement that is not related to the vibration alarm being measured will affect the accelerometer readings much when test signals of between 10 and 40 ms are used since these short intervals would require non-alarm signal oscillatory activity that is over 25 Hz (i.e. 1000 ms/40) to occur, which is much faster than that of endogenous movement of the human body or of forces that are normally applied to the human body during daily life. Test criteria can be applied to the individual maxima and minima rather than to the difference measure "delta" and the criteria can be applied to sequentially, for example, M number of positive and negative data values must be above specified set of values which increase or decrease when the criteria is related to the onset or offset of an alarm signal.

Paired Pulse Criteria:

When the alarm test uses 2 sequential pulses of different strengths, separated by a pause, then the increase within a particular axis may be compared to a paired-pulse intra-axis value and the difference between these two values must meet a paired-pulse intra-axis threshold criterion. When values from 2 or more axes are compared then this result is compared to a paired-pulse inter-axis value using a paired-pulse inter-axis criterion. Paired pulse designs may be used to examine non-linear characteristics in a motor's performance, or to obtain two estimates when the motor is on and is in two different states of motion. When more than 1 pulse is used, then the accelerometer results for two or more pulses may be combined when evaluating the vibration test. For example, only one pulse can be required to produce a change in the accelerometer that meets a threshold criterion (i.e. the maximum result is used), or all the pulses must all pass the threshold test. Numerous variations in the evaluation of test results are obviously also possible.

Age/Usage Based Criteria and Criteria Correction:

Threshold values can be determined during calibration which occurs at time of manufacture, at time of implantation, or at subsequent calibration periods that are accomplished during doctor visits or automatically by the device at specific intervals. Additionally, the thresholds can be adjusted according to the amount of use that a transducer, such as a vibration module, has experienced. For example, as the module ages or is used, an expected change in vibration strength or frequency may occur and only deviations from this expected change may cause a vibration-failure event to occur. An alert-failure event may require that the vibration voltage be increased by a specified amount. If this is the case then the medical professional may adjust the vibration to the intended level and then reset the threshold criteria. Alarm test results can be compared to those obtained during a calibration profile operation which occurs either at the factory, or during an initial patient visit after IMD 3 is implanted.

Intra- and Inter-Axis Criteria:

These two types of criteria may be used independently or jointly to create alarm-test results. When the alarm test uses a single pulse which is compared to a baseline reference value then the increase within a particular axis may be compared to a intra-axis threshold criterion, while when values from 2 or more different axes are compared then this result is compared to an inter-axis threshold criterion. An inter-axis threshold criterion may require that that values assessed in the x-axis are within a specified range of those measured in the y-axis, in order to ensure that the motor is providing circular motion. If the two axes produce different vibration strengths, or if this difference changes over time, then this may suggest that there is something wrong with the motor.

Alarm-Test Criteria Related to Complex Alarm-Test Signals:

The alarm test threshold criteria values may be constant for a single discrete drive signal (e.g. single pulse), for a series of pulses of the same shape, or may change for series that use different shapes, utilize test signals having linear or arbitrary functions (continuous or discontinuous). Two or more functions can be used as alarm test signals such as two voltage functions with two different slopes (e.g. 2× and 4×) and each test signal will be evaluated with a different criterion. A single pulse which ramps from 3.0 to 3.6 volts may be used as an alarm test signal. In some embodiments, a specified voltage will cause the motor to vibrate at a particular speed. DC-motors are often designed to increase in speed as the DC voltage increases. A voltage by frequency, or voltage by vibration, magnitude function may be derived and assessed with alarm-test criteria. When AC motors are used, then the characteristics of the AC signal, (e.g., voltage, AC frequency) can be used in the evaluation of the resulting alarm test data measurements of vibration frequency or amplitude.

Overview

The alarm test methods and systems can be incorporated into many types of implantable, or semi-implantable, medical devices. These can also be realized by independent modules which can be self-powered and which are implanted separately within a patient. These may be stand-alone alarm-testing modules that monitor alerts created by other devices, or can be modules that contain both alerting and monitoring capacity and which communicate with other medical devices implanted in the patient. Alarm-testing devices can be realized by physically attaching these to the housing of a medical monitoring and/or treatment device that provides patient alerting.

Figure 10B:
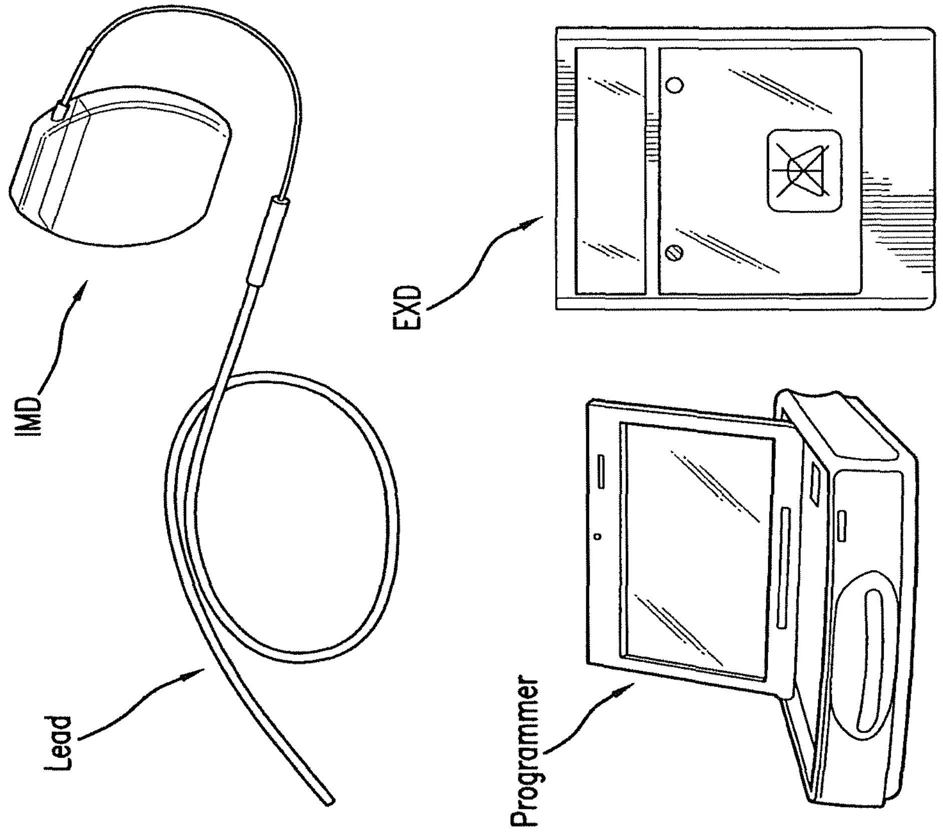
FIGS. 10A and 10B illustrate the components of an exemplary medical monitoring system in which the alarm testing can be realized and which in this example is the Guardian™ monitoring system.
Figure 10A:
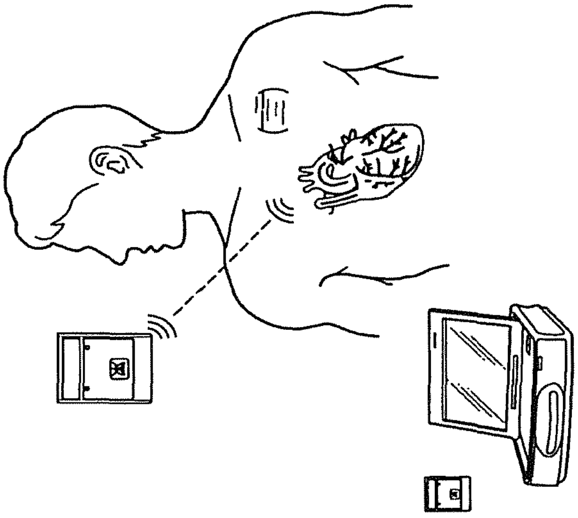

FIGS. 10A and 10B show the components of an exemplary medical monitoring system in which the alarm testing can be realized. In this example, the Angel-Medical Guardian™ monitoring system is shown which has both internal and external patient alerting capacity. The left side of the figure labeled "A" illustrates schematically the Angel-Medical Guardian™ monitoring system which can be the medical system shown in FIG. 1. The figure shows a patient with an IMD 3 having a lead that is inserted into a patient's heart. The EXD 20 communicates wirelessly with the IMD 3 and may also communicate with the physician's programmer using wired or wireless means (in the figure the EXD is shown communicating with the programmer by means of a cable). On the right side of the figure, an actual system is shown and includes the IMD, lead, and external equipment including an EXD and programmer, while a remote medical center, which can be contacted from the EXD via a cellular network, is not shown.

Figure 11:
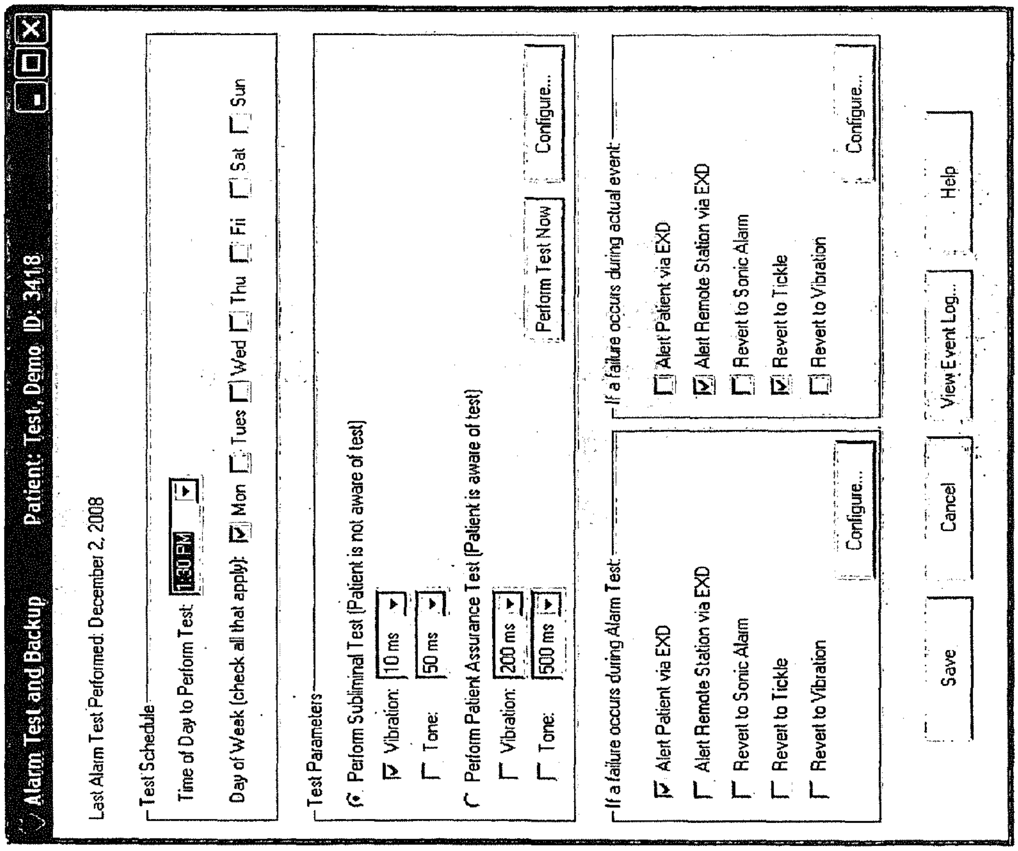
FIG. 11 is an example of an alarm test programming screen which is presented to a medical professional in order to configure and calibrate the alarm testing that occurs in the device.

FIG. 11 shows the type of screen which must be used to configure the alarm-tests in actual clinical practice. This screen is presented to a medical practitioner during the programming of the IMD when the IMD is programmed just after implantation or during subsequent visits by the patient during which data is uploaded from the IMD and the IMD is tested. The top of the Screen shows the patient's unique ID which here is 3418. The screen displays information as to the time the last test was performed under control of a physician's programmer (which often should be less than 12 months, and preferably at least every 6 months). Because the patient may not go to the same doctor's office on different visits, the data on which the last alarm test was performed under control of a patient programmer is uploaded from the event log of the IMD memory 116. While this information is also available in the alarm-test module 28 of the EXD, this is not used to populate this field because EXDs can be lost and the record in the IMD will be more complete. The "Text Schedule" sub-panel allows the medial professional to schedule the time of day that the alarm-test occurs as well as the day of the week. Although the test can be done less than once per week, Angel-Medical currently prefers that the alarm is tested at least once a week so this sub-panel is configured for weekly testing. The "Test Parameters" sub-panel allows the medical personnel to determine if the test is performed using a 'subliminal' mode, which uses relatively short alarm test signals, or a 'patient assurance' mode which allows the patient to notice the alarm test. Next to the vibration and sound check-box options are drop-down menus that allow the medical professional to adjust, within an allowed range, the specific duration which will be used for an alarm test. The "perform test now" button causes an alarm-test to be conducted with the selected parameters and these parameters and the results are then stored in the alarm-test modules 24, 28, and the memory module 116 of the IMD. Although the "perform test now" button will allow alarm-testing to occur, the alarm testing also may occur automatically when the programmer first communicates with the IMD 3 during a doctor's visit, if this is defined in the programmers default communication protocol. The "configure" button will invoke a separate screen in which the alarm test parameters may be further configured. For instance, in the case of the vibration alarm test signal the 10 ms test signal can be configured to be repeated 2 or 3 times and the results from all repetitions are used to determine whether alarm test pass or alarm test failure results have occurred. In the case of the tone alarm-test, the volume, repetition rate, test frequencies, and number of repetitions may be configured. The "If a failure occurs during an Alarm Test" sub-panel determines what actions to take during failure, such as immediately alerting the EXD of such a failure. Additionally, the IMD may revert to a sonic alarm if the default alarm is a vibration alarm, or vice-versa, using the check-boxes. The "configure" button allows the user to adjust and design more additional alarm-failure features such as attempting re-tests before deciding an alarm test has failed. The "if a failure occurs during actual event" is a sub-panel that determines what to do if the alarm-test fails when an actual alert signal fails to be evoked, for example, in response to the detection of a medical event. This panel therefore serves to design the "back-up" alarm. Additional settings may be adjusted using the "configure" button as have been described previously. The Save button allows the current settings and preferences to be saved both in the Programmer, the IMD, and the EXD. The "View Event Log" button allows the medical practitioner to view the event logs of the IMD, the EXD, and the Physician programmer. This information includes graphs of the historical alarm alarm-test results in order to determine if the IMD and EXD are functionally correctly and as expected. The "Cancel" and "Help" buttons allow the medical practitioner to cancel operations or view help screens as is conventionally practiced. The particular embodiment of the alarm test and backup window shown in FIG. 11 is shown for illustration and can obviously include other features, such as allowing for design of the alarm-testing which occurs in the EXD 20. However, this is not practiced in the example shown.

The alarm test protocols described here can be implemented by the processor of the IMD 3, or may be appropriately modified to be realized by the processor 54 and alarm test module 28 of the EXD 20. The IMD 3 alarm test module 120 can be implemented as an actual module 120 as shown here, or may be realized using the operating program of the IMD 3 processor 100 and alarm test parameters stored in the IMD 3 memory 116 so that the alarm tests are carried out as intended. The modules of FIG. 2 can operate to measure data which is presented in FIGS. 3-6, and can evaluate the alarm test data to realize alarm test results that are then used to guide operation of the system 12. The methods depicted in FIGS. 7-9 may be applied to alarm testing of alarm signals that cue to patient with visual, sonic, vibratory, pain, or other types of cues, and for alarm related operations that require communication between the IMD 3, EXD 20, physician programmer 18, and remote diagnostic center 22.

The terms "alerting", "alarming", and "patient notification" are generally used interchangeably in this material. This disclosure describes illustrative embodiments which do not limit the invention. The configuration of the system, the number of components, and the function of the components can be modified and still serve to realize the advantages of the invention as described herein. The steps of the processes and methods may assume a slightly different order without departing from the intended results which have been described, and loops from later steps to earlier steps may occur at other steps in the process. The modules and steps described herein may be implemented by software or hardware since these will produce equivalent results. Although the modules of FIG. 2 are shown as discrete components, portions of modules that perform similar functions may be shared between modules. The titles (e.g., "Overview") used to name different sections of this disclosure are meant for organizational purposes only and are not meant to be limiting in any manner.

What is claimed is:

1. An implanted device comprising:

a vibrator, the vibrator including a drive motor and a drive circuit;

an accelerometer coupled to said vibrator and configured for sensing alarm test data related to movement of the vibrator;

a power source for providing electricity to the implanted device;

a processor configured for bi-directional wireless communication, the processor configured to:

receive a command from an external device to perform an alarm test;

perform the alarm test and analyze the alarm test data in order to generate alarm test results, and, communicate the alarm test results to the external device.

2. The system of claim 1, in which the sensed alarm test data are reflective of the speed of rotation.

3. The system of claim 1, in which the sensed alarm test data are reflective of the amplitude of vibration.

4. The system of claim 1, in which the alarm test results indicate either a pass or fail status.

5. The system of claim 1, in which the alarm test results contain measurements of the alarm test data.

6. The system of claim 1, in which the alarm test results contain summaries of measurements of the alarm test data.

7. The system of claim 1, in which the external device is a patient programmer.

8. The system of claim 1, in which the external device is an external alarm system device.

9. The system of claim 1, in which the external device is a device to provide communication between the implanted device and a remotely located computer or service.

10. The system of claim 1, wherein the processor is further configured to adjust a characteristic of electricity that is received by the drive circuit to adjust the drive in order to adjust vibration, the adjusting occurring according to a characteristic of the alarm test results.

11. The system of claim 1, wherein the processor is further configured to adjust a characteristic of electricity that is received by the drive circuit, the characteristic being a drive voltage pattern that is received by the drive circuit to adjust the drive and promote vibration to occur at a selected amplitude.

12. The system of claim 1, wherein the processor is further configured to adjust a characteristic of electricity that is received by the drive circuit, the characteristic being a time duration of the drive voltage that is provided to the drive circuit to adjust the drive and promote vibration to occur at a selected amplitude.

13. The system of claim 1, wherein the external device is further configured to receive and process an alarm test result sent by the implanted device.

14. The system of claim 1, wherein the processor is further configured to provide electrical stimulation of a patient's heart.

15. The system of claim 1, wherein the processor is further configured to provide electrical monitoring of a patient's heart.

16. The system of claim 1, wherein the processor is further configured to provide monitoring a signal related to a medical condition of a patient.

17. The system of claim 1, wherein the processor is further configured to provide monitoring a signal related to a medical condition of a patient's brain.

18. The system of claim 1, wherein the processor is further configured to provide drug to a patient.

19. The system of claim 1, wherein the processor is further configured to permit a patient to initiate an alarm test operation using an external device.

20. The system of claim 1, wherein the processor is further configured to permit a care giver to initiate an alarm test operation using an external device.

21. The system of claim 1, wherein the processor is further configured to permit alarm test parameters to be programmably adjusted according to signals received from the external device.

* * * * *